(12) United States Patent
Velliquette et al.

(10) Patent No.: US 11,312,754 B2
(45) Date of Patent: Apr. 26, 2022

(54) SUNFLOWER SEED PROTEIN-DERIVED PEPTIDES

(71) Applicant: ACCESS BUSINESS GROUP INTERNATIONAL LLC, Ada, MI (US)

(72) Inventors: Rodney A. Velliquette, Ada, MI (US); Eugene Maly, Kentwood, MI (US)

(73) Assignee: ACCESS BUSINESS GROUP INTERNATIONAL LLC, Ada, MI (US)

(*) Notice: Subject to any disclaimer, the term of this patent is extended or adjusted under 35 U.S.C. 154(b) by 0 days.

(21) Appl. No.: 16/884,603

(22) Filed: May 27, 2020

(65) Prior Publication Data
US 2021/0017240 A1    Jan. 21, 2021

Related U.S. Application Data

(60) Provisional application No. 62/913,386, filed on Oct. 10, 2019, provisional application No. 62/855,168, filed on May 31, 2019.

(51) Int. Cl.
| | |
|---|---|
| *A61K 38/07* | (2006.01) |
| *A61K 38/08* | (2019.01) |
| *A61K 45/06* | (2006.01) |
| *A61K 9/00* | (2006.01) |
| *A61P 29/00* | (2006.01) |
| *A61P 39/06* | (2006.01) |
| *C07K 14/415* | (2006.01) |
| *C07K 5/107* | (2006.01) |
| *A23L 33/18* | (2016.01) |
| *A23L 2/66* | (2006.01) |

(52) U.S. Cl.
CPC .............. *C07K 14/415* (2013.01); *A23L 2/66* (2013.01); *A23L 33/18* (2016.08); *A61K 9/0014* (2013.01); *A61K 9/0056* (2013.01); *A61K 38/07* (2013.01); *A61K 38/08* (2013.01); *A61K 45/06* (2013.01); *A61P 29/00* (2018.01); *A61P 39/06* (2018.01); *C07K 5/1016* (2013.01); *A23V 2002/00* (2013.01)

(58) Field of Classification Search
CPC .......... A23L 2/66; A23L 33/18; A23L 33/185; A61K 38/011; A61K 38/07; A61K 38/08; A61K 45/06; A61K 9/0014; A61K 9/0056; A61P 29/00; A61P 39/06; C07K 14/415; C07K 5/1016; C07K 5/107
See application file for complete search history.

(56) References Cited

U.S. PATENT DOCUMENTS

| | | | |
|---|---|---|---|
| 5,989,600 A | 11/1999 | Nielsen et al. | |
| 6,036,983 A | 3/2000 | Nielsen | |
| 6,372,282 B1 | 4/2002 | Edens et al. | |
| 6,372,452 B1 | 4/2002 | Millan Rodriguez et al. | |
| 6,465,209 B1 | 10/2002 | Blinkovsky et al. | |
| 6,838,100 B2 | 1/2005 | Jaeger et al. | |
| 7,056,714 B2* | 6/2006 | Rosazza | C07H 21/04 435/189 |
| 8,048,652 B2 | 11/2011 | Fichtali et al. | |
| 8,062,862 B2 | 11/2011 | Fritsche et al. | |
| 8,728,556 B2 | 5/2014 | Schmitt et al. | |
| 8,815,806 B2 | 8/2014 | Aluko et al. | |
| 9,034,402 B2 | 5/2015 | Wong et al. | |
| 10,023,633 B2* | 7/2018 | Laeremans | C07K 16/28 |
| 10,706,955 B2* | 7/2020 | Bremel | G16B 20/30 |
| 2009/0042809 A1 | 2/2009 | Edens et al. | |
| 2011/0165635 A1 | 7/2011 | Copenhaver et al. | |
| 2016/0222058 A1 | 8/2016 | Wu et al. | |
| 2018/0110722 A1 | 4/2018 | Velliquette et al. | |
| 2019/0032102 A1 | 1/2019 | Lynglev | |

FOREIGN PATENT DOCUMENTS

| | | |
|---|---|---|
| WO | 2015048332 A2 | 4/2015 |
| WO | 2017147060 A9 | 9/2017 |

OTHER PUBLICATIONS

UniProt Q9HBD8, pp. 1-3. Integrated into UniProtKB/TrEMBL on Mar. 1, 2001. (Year: 2001).*
UniProt A0A0A8YLD5, pp. 1-2. Integrated into UniProtKB/TrEMBL on Mar. 4, 2015. (Year: 2015).*
UniProt A0A5K1FIM7, pp. 1-2. Integrated into UniProtKB/TrEMBL on Dec. 11, 2019. (Year: 2019).*
Chalamaish et al. Immunomodulatory and anticancer protein hydrolysates (peptides) from food proteins: A review. Food chemistry, 2018, 245, 205-222.
Alvaro Villanueva et al., "Peptide characteristics of sunflower protein hydrolysates", Journal of the American Oil Chemists' Society (JAOCS), vol. 76, No. 12, Dec. 1, 1999, pp. 1455-1460.
Megias, C., et al., "Purification of an ACE inhibitory peptide after hyrolysis of sunflower (*Helianthus annus* L.) protein isolates", Journal of Agricultural and Food Chemistry, American Chemical Society, Books and Journals Division, vol. 52, No. 7, Apr. 7, 2004, pp. 1928-1932.

(Continued)

*Primary Examiner* — Julie Ha
(74) *Attorney, Agent, or Firm* — Warner Norcross + Judd LLP

(57) ABSTRACT

A protein hydrolysate composition is provided. The protein hydrolysate composition comprises isolated peptides useful for ameliorating a condition of a subject. Compositions comprising the protein hydrolysate composition are also provided. The compositions may be adapted for oral or topical administration to the subject, and may compose a foodstuff or beverage (e.g. a medical food), a topical composition (e.g. a lotion, cream, etc.), a kit, and the like. A methods of ameliorating the condition of the subject is further provided. The method include administering the protein hydrolysate composition to the subject. The method may be useful in reducing blood pressure, inflammation, reduced immunity, and/or oxidative stress in the subject.

15 Claims, 15 Drawing Sheets
Specification includes a Sequence Listing.

(56) References Cited

OTHER PUBLICATIONS

Peng Luo et al., "Preparation of liposome encapsulating angiotensin-I-converting enzyme inhibitory peptides from sunflower protein hydrolysates", Molecular Medicine Reports, vol. 17, Jan. 24, 2018, pp. 5306-5311.
Database UniProt [Online] Oct. 1, 2003, "SubName: Full=Vicilin seed storage protein {ECO:0000313 EMBL: AAM54366.1); Flags: Fragment;", Database accession No. Q7Y1C1.
International Search Report for Application No. PCT/US2020/035093 dated Nov. 30, 2020, 8 pages.

\* cited by examiner

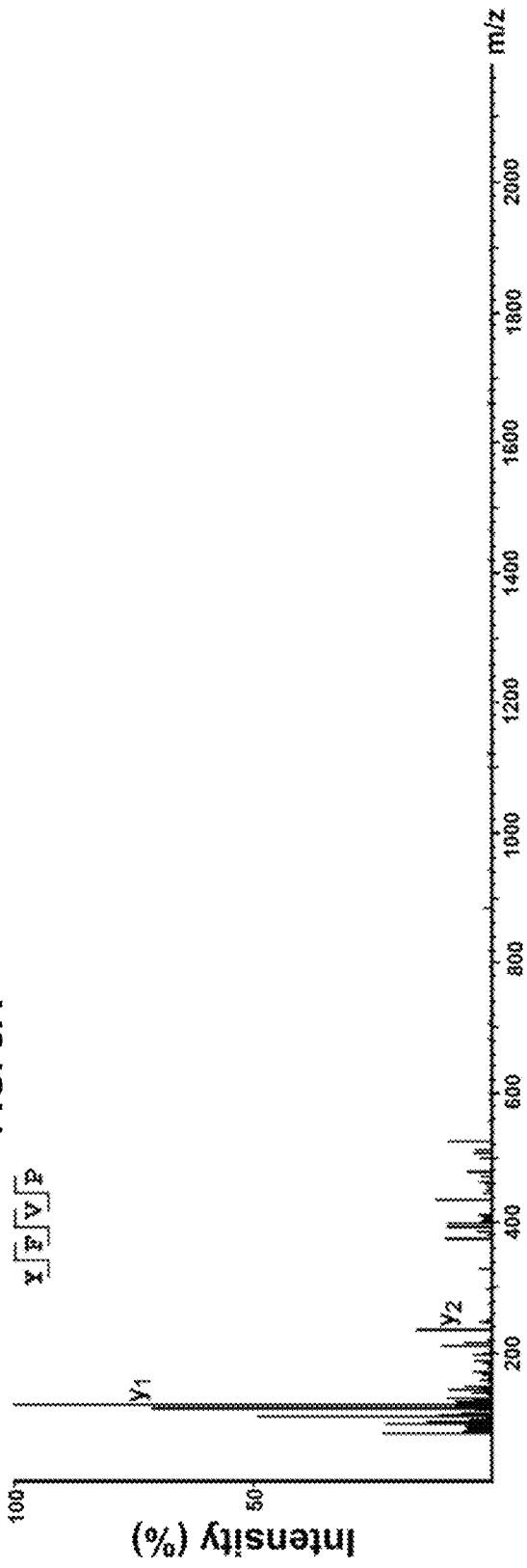
FIG. 3A
FIG. 3B
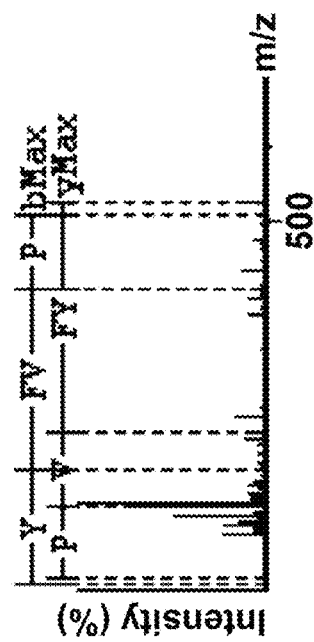
FIG. 3C
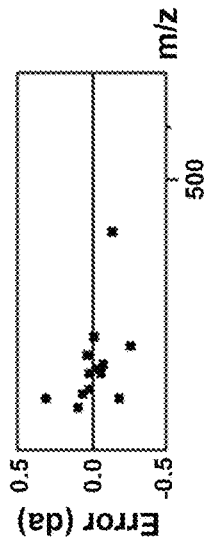
FIG. 3D

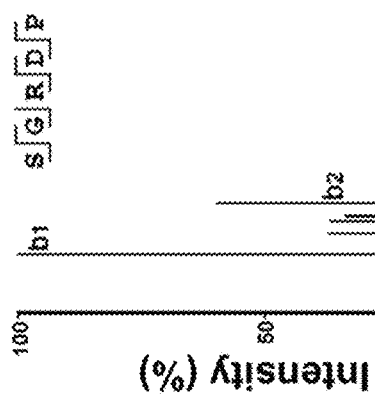
FIG. 4A
FIG. 4B
| # | b | b-H2O | b-NH3 | b (2+) | Seq | y | y-H2O | y-NH3 | y (2+) | # |
|---|---|---|---|---|---|---|---|---|---|---|
| 1 | 88.06 | 70.03 | 71.01 | 44.52 | S | | | | | 5 |
| 2 | 145.08 | 126.96 | 127.68 | 73.03 | G | 444.22 | 426.19 | 427.19 | 222.61 | 4 |
| 3 | 301.39 | 283.15 | 284.14 | 151.08 | R | 387.20 | 369.19 | 370.17 | 194.10 | 3 |
| 4 | 415.95 | 398.18 | 399.16 | 208.44 | D | 231.10 | 213.09 | 214.07 | 116.04 | 2 |
| 5 | | | | | P | 116.04 | 97.92 | 98.71 | 58.54 | 1 |
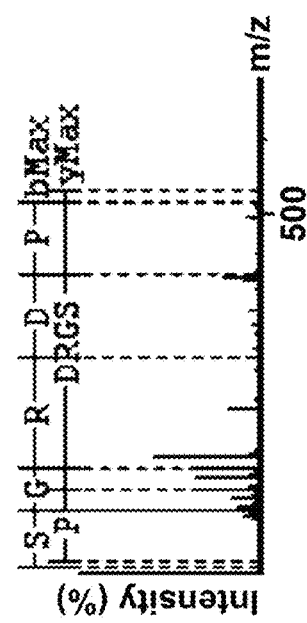
FIG. 4C
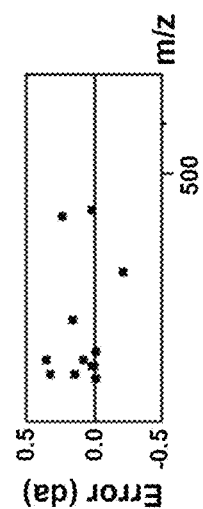
FIG. 4D

FIG. 5A
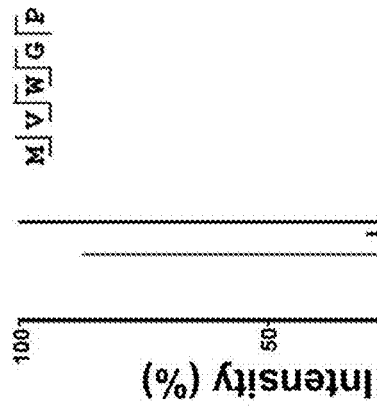
| # | b | b-H2O | b-NH3 | b (2+) | Seq | y | y-H2O | y-NH3 | y (2+) | # |
|---|---|---|---|---|---|---|---|---|---|---|
| 1 | 132.23 | 114.00 | 114.72 | 66.52 | M | | | | | 5 |
| 2 | 231.42 | 213.11 | 214.09 | 116.04 | V | 458.24 | 440.23 | 441.21 | 229.62 | 4 |
| 3 | 417.39 | 399.19 | 400.17 | 209.04 | W | 359.43 | 341.16 | 342.14 | 180.09 | 3 |
| 4 | 474.22 | 456.21 | 457.19 | 237.61 | G | 173.28 | 155.52 | 156.48 | 86.64 | 2 |
| 5 | | | | | P | 116.04 | 98.06 | 99.04 | 58.54 | 1 |
FIG. 5B
FIG. 5C
FIG. 5D (A) Untreated    (B) IL-4/GM-CSF    (C) Fraction 7

(A) Untreated (B) IL-4/GM-CSF (C) Fraction 7

(A) Untreated (B) IL-4/GM-CSF (C) Fraction 7

SEQUENCE LISTING

```
<160> NUMBER OF SEQ ID NOS: 5

<210> SEQ ID NO 1
<211> LENGTH: 4
<212> TYPE: PRT
<213> ORGANISM: Helianthus annuus

<400> SEQUENCE: 1

Tyr Phe Val Pro
1

<210> SEQ ID NO 2
<211> LENGTH: 5
<212> TYPE: PRT
<213> ORGANISM: Helianthus annuus

<400> SEQUENCE: 2

Ser Gly Arg Asp Pro
1               5

<210> SEQ ID NO 3
<211> LENGTH: 5
<212> TYPE: PRT
<213> ORGANISM: Helianthus annuus

<400> SEQUENCE: 3

Met Val Trp Gly Pro
1               5

<210> SEQ ID NO 4
<211> LENGTH: 9
<212> TYPE: PRT
<213> ORGANISM: Helianthus annuus

<400> SEQUENCE: 4

Thr Gly Ser Tyr Thr Glu Gly Trp Ser
1               5

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
        oligonucleotide

<400> SEQUENCE: 5
gtgactcagc a                                                              11
```

SUNFLOWER SEED PROTEIN-DERIVED PEPTIDES

CROSS-REFERENCE TO RELATED APPLICATIONS

This application claims priority to U.S. Pat. Appl. No. 62/855,168, filed on 31 May 2019, and U.S. Pat. Appl. No. 62/913,386, filed on 10 Oct. 2019, the contents of which are incorporated by reference.

SEQUENCE LISTING

This application contains a Sequence Listing, which has been submitted electronically in ASCII format and is hereby incorporated by reference in its entirety. The ASCII copy, created on 15 May 2020, is named 018716_188625-US_WN3395_P1_SL.txt and is 1,036 bytes in size.

FIELD OF THE INVENTION

The present invention relates to protein hydrolysate compositions and, more specifically, to protein hydrolysate compositions derived from sunflower seed proteins, compositions comprising the protein hydrolysate compositions, and methods of ameliorating conditions with the protein hydrolysate compositions.

BACKGROUND OF THE INVENTION

It is estimated that approximately 70% of the human immune system is in close contact with mucosal tissues and, primarily, the gastro-intestinal tract, in order to closely monitor the vast numbers of microorganisms that inhabit the gut, as well as to maintain intestinal homeostasis. For example, one function of the mucosal immune system is to initiate an adaptive immune response upon exposure to a pathogenic organism. Unfortunately, however, such immune responses produced in response to disruption of intestinal homeostasis (e.g. resulting from western diet, gluten sensitivity, leakage of microbial components, etc.) may result in inflammation, and thus lead to and/or exacerbate inflammatory conditions such as colitis, IBD, etc.

For example, the first line of defense against pathogens in the vertebrate innate immune system includes differentiated cells (e.g. myeloid cells) with particular functions, such as monocytes that produce pro-inflammatory cytokines and chemokines to recruit leukocytes to an infection site and amplify an inflammatory response. This cytokine/chemokine production occurs upon activation of NFκB and pattern recognition receptors (PRR) expressed by the monocyte, with the PRR being recognizing pathogens and being activated by engagement therewith. Monocytes also function as a circulating reservoir of undifferentiated macrophages and myeloid lineage dendritic cells (DCs). When homeostasis is perturbed, monocytes are recruited to sites of inflammation and differentiate into DCs, which function as a primary type of antigen-presenting cell and play a primary role in initiating activation of adaptive immune response by translating early pathogen-induced response into memory response. More specifically, monocytes link innate immunity to adaptive immunity by increasing expression of co-stimulatory receptors (e.g. CD40, CD80, CD86, which greatly enhance T-cell activation potential) during differentiation, as well as by upregulating chemotactic receptors (e.g. CCR7) that induce DCs to travel to a lymph node or the spleen and present antigens to T-cells.

Peptides are short chains of amino acids that may be synthesized (e.g. biologically and/or synthetically) or derived from intact proteins (e.g. via enzymatic and/or chemical degradation). Certain peptides are bioactive and may provide physiological benefits to the health of humans and/or other animals. Such bioactive peptides may be naturally occurring, including some which are latent in intact proteins and released via enzymatic hydrolysis from the parent food proteins, e.g. in vitro and/or in vivo. For example, milk (e.g. a parent food) is known to contain many bioactive proteins and peptides, including lactoferrin, caseins, colostrums, etc., which are thought to induce biological effects (e.g. antihypertensive effects) via enzyme activation and/or inhibition.

BRIEF SUMMARY OF THE INVENTION

A protein hydrolysate composition is provided. The protein hydrolysate composition comprises isolated peptides useful for ameliorating a condition of a subject. In certain embodiments, the isolated peptides are derived from sunflower seed protein.

Functional compositions comprising the protein hydrolysate composition are also provided. In some embodiments, the functional composition is a foodstuff or beverage composition adapted for oral consumption. In particular embodiments, the functional composition is a topical composition adapted for topical administration.

A method of ameliorating a condition of the subject is further provided. The method comprises administering the protein hydrolysate composition the subject, and may be used to ameliorate a variety of conditions such as those involving high blood pressure, inflammation, oxidative stress, and/or reduced immunity.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the steps or components set forth in the following description or illustrated in the drawings. It is to be understood that the phraseology and terminology used herein are for the purpose of description and should not be regarded as limiting.

BRIEF DESCRIPTION OF THE DRAWINGS

FIGS. 3A-3D provide amino acid sequence data for an isolated peptide "YFVP" as SEQ ID NO: 1, with a mass spectrum of a fraction of the protein hydrolysate composition shown in FIG. 3A as well as a corresponding ion table shown in FIG. 3B, fragment map shown in FIG. 3C, and mass error mapping shown in FIG. 3D.

FIGS. 4A-4D provide amino acid sequence data for an isolated peptide "SGRDP" as SEQ ID NO: 2, with a mass spectrum of a fraction of the protein hydrolysate composition shown in FIG. 4A as well as a corresponding ion table shown in FIG. 4B, fragment map shown in FIG. 4C, and mass error mapping shown in FIG. 4D.

FIGS. 5A-5D provide amino acid sequence data for an isolated peptide "MVWGP" as SEQ ID NO: 3, with a mass spectrum of a fraction of the protein hydrolysate composition shown in FIG. 5A as well as a corresponding ion table shown in FIG. 5B, fragment map shown in FIG. 5C, and mass error mapping shown in FIG. 5D.

FIG. 12 discloses SEQ ID NOS 1-4, respectively, in order of appearance.

FIG. 13 discloses SEQ ID NOS 1-4, respectively, in order of appearance.

FIG. 14 discloses SEQ ID NOS 1-4, respectively, in order of appearance.

DETAILED DESCRIPTION OF THE INVENTION

Figure 1:
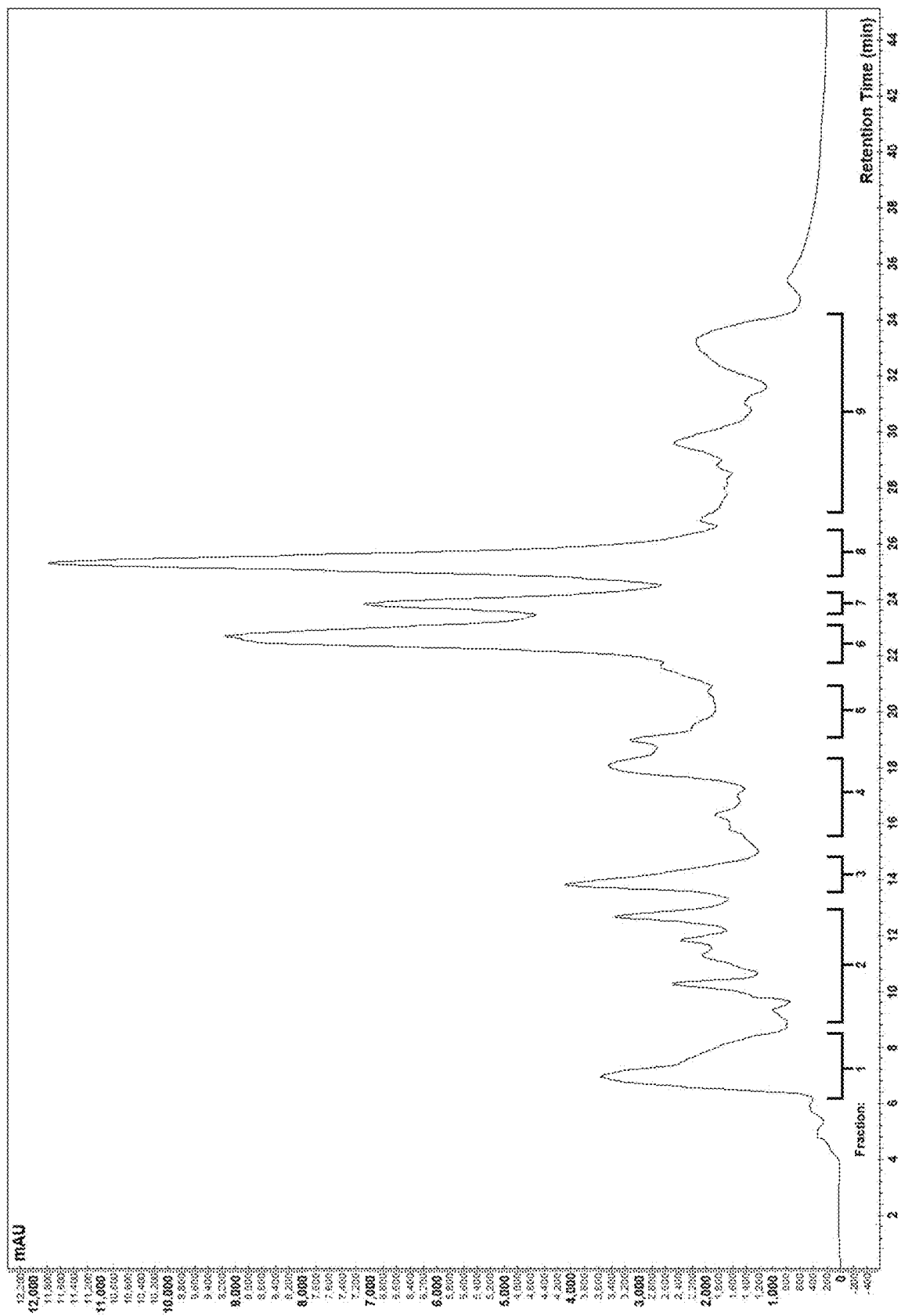
FIG. 1 provides a high performance liquid chromatography (HPLC) profile of a crude protein hydrolysate prepared in accordance with the subject disclosure.

In general, this disclosure provides a protein hydrolysate and methods relating to the formulation and use of the same. The protein hydrolysate composition has improved characteristics, which, as illustrated by the Examples, may be utilized in ameliorating a condition of a subject, e.g. by reducing blood pressure, inflammation, immunity reduction, and/or oxidative stress in the subject upon administration of the protein hydrolysate composition thereto.

The protein hydrolysate composition comprises one or more certain isolated peptides, which are described in detail below. As will be understood in view of this disclosure, the protein hydrolysate composition is not particularly limited aside from the isolated peptides and related components and methods.

As used herein, the term "protein hydrolysate" refers to a reaction product produced via chemical and/or enzymatic digestion (e.g. enzyme-mediated hydrolysis) of a protein or fermentation of a protein. As understood in the art, such protein hydrolysates typically comprise peptides, amino acids, and other particular reaction products that are hydrolytically derived from the protein and/or other materials (e.g. such as when a protein fermentation is hydrolyzed). Similarly, as used herein, the term "peptide" refers to a molecule having 2 or more amino acids that are joined together by a peptide bond. As will be understood by those of skill in the art, the term "peptide" encompasses oligopeptides (i.e., peptides comprising 20 or fewer, optionally 10 or fewer amino acids, e.g. di-, tri-, tetra-, and pentapeptides, etc.) polypeptides (i.e., peptides comprising greater than 10, optionally greater than 20 amino acids), proteins (i.e., organic compounds comprising amino acids linked via peptide bonds in a linear chain and folded into a globular form), enzymes (i.e., functional proteins), and the like, which may be modified (e.g. naturally and/or synthetically via glycosylation, acetylation, phosphorylation, etc.), branched, etc. Such peptides may include any known amino acid, such as the 20 gene-encoded amino acids, as well as other natural and/or synthetic amino acids (e.g. selenocysteine, etc.). However, it is to be appreciated that synthetic compositions comprising substantially the same components of a natural-protein derived hydrolysate, in accordance with the description and limitations herein, may also be utilized. As such, it is to be appreciated that the peptides described herein may be produced recombinantly, synthetically, semi-synthetically, and/or obtained from natural sources (e.g. via isolation after hydrolysis of a protein and/or enzyme). Moreover, the term "peptides" may be used in the plural sense in reference to more than one peptide molecule, or in a collective sense in reference to two or more distinct peptides (e.g. which differ from each other in terms of structure, function, etc.), or both. The term "peptides" is not intended to be limited to the latter sense described above, but instead is meant to refer to any one or more groups of particular peptide molecules.

As introduced above, the protein hydrolysate composition comprises isolated peptides. As used herein with respect to peptides, and otherwise as designated, the term "isolated" refers to material that has been removed from its original environment. For example, a naturally-occurring protein or peptide present in a living animal is not isolated, but the same peptide, which is separated from some or all of the coexisting materials in the natural system, is "isolated". Additionally, a small peptide that is prepared by chemically altering a naturally-occurring protein or peptide (e.g. via hydrolysis, etc.) is also isolated in this regard, as such a small peptide is removed from its original environment (e.g. as part of the naturally-occurring protein or peptide). It is to be understood that such isolated peptides may compose part of a composition and still be isolated in that the composition is not part of its natural environment. However, one of skill in the art will readily appreciate that one or more, alternatively, all, of the isolated peptides may be synthetically prepared and utilized in the composition, such that, while the present embodiments detail and describe a hydrolysate, the protein hydrolysate composition may equally be prepared from and/or comprise synthetic peptides, hydrolysate-derived peptides, or combinations thereof. With regard to the present embodiments, the protein hydrolysate composition comprises an isolated peptide having the sequence of at least one of Tyr-Phe-Val-Pro (YFVP; SEQ ID NO: 1), Ser-Gly-Arg-Asp-Pro (SGRDP; SEQ ID NO: 2), Met-Val-Trp-Gly-Pro (MVWGP; SEQ ID NO: 3), and Thr-Gly-Ser-Tyr-Thr-Glu-Gly-Trp-Ser (TGSYTEGWS; SEQ ID NO: 4). One of skill in the art readily understands that the three-letter and one-letter abbreviations of these peptide sequences correspond to the amino acids tyrosine (Tyr, Y), phenylalanine (Phe, F), valine (Val, V), proline (Pro, P), serine (Ser, S), glycine (Gly, G), arginine (Arg, R), aspartic acid (Asp, D), methionine (Met, M), tryptophan (Trp, W), treonine (Thr, T), and glutamic acid (Glu, E), respectively.

In some embodiments, the protein hydrolysate composition comprises isolated peptides having the sequence of at least two, optionally of at least three of SEQ ID NO: 1, SEQ ID NO: 2, SEQ ID NO: 3, and SEQ ID NO: 4. In specific embodiments, the protein hydrolysate composition comprises isolated peptides of SEQ ID NO: 1, SEQ ID NO: 2, SEQ ID NO: 3, and SEQ ID NO: 4. Accordingly, as used herein, reference to "the isolated peptides" is to be understood to include any two or more peptide molecules having the sequence of SEQ ID NO: 1, SEQ ID NO: 2, SEQ ID NO: 3, and/or SEQ ID NO: 4, subject to the limitations and requirements described herein.

In general, the isolated peptides of the protein hydrolysate composition are typically prepared via hydrolysis of a protein material. More specifically, the isolated peptides and/or the protein hydrolysate composition itself may be prepared, at least in part, by hydrolyzing the protein material. Accordingly, a method of preparing the protein hydrolysate composition is also provided, and includes hydrolyzing the protein material to give the isolated peptides, thereby preparing the protein hydrolysate composition.

The protein material is not limited, and may be any material comprising proteins and/or peptides comprising amino-acid sequences corresponding to SEQ ID NO: 1, SEQ ID NO: 2, SEQ ID NO: 3, and SEQ ID NO: 4 and capable of being hydrolyzed to give peptides having sequences corresponding to SEQ ID NO: 1, SEQ ID NO: 2, SEQ ID NO: 3, and SEQ ID NO: 4.

Typically, the protein material is a sunflower seed protein material (i.e., is a material comprising proteins and/or peptides obtained from a seed produced by a plant of genus Helianthus). A variety of sunflower seed protein materials may be used in the process to preparing the protein hydrolysate composition. In general, the sunflower seed protein material may be prepared, derived, or otherwise obtained from sunflower seeds. The sunflower seeds may be obtained from natural sunflowers (i.e., non-genetically modified), genetically modified sunflowers, or combinations thereof, and may be whole or processed (e.g. shelled, dried, ground, etc.). Examples of suitable sunflower seed protein materials obtained from such seeds include sunflower seed extracts, sunflower meals, sunflower seed powders, sunflower seed flours, isolated sunflower seed proteins (e.g. protein isolates), sunflower seed protein concentrates, and the like, as well as derivatives, modifications, and combinations thereof. In certain embodiments, the sunflower seed protein material may be processed, and thus, for example, may comprise or be a defatted, partially defatted, ground, dried, precipitated, washed, filtered, or mesh-sorted sunflower seed protein material, or a combination thereof.

In some embodiments, the sunflower seed protein material comprises a protein content of at least 15, optionally of at least 25, optionally at least 35, optionally of at least 50 wt. %. In specific embodiments, the sunflower seed protein material comprises a protein content of from 30 to 99 Wt. %, such as from 35 to 95, optionally from 35 to 90, optionally from 40 to 90, optionally from 40 to 85, optionally from 40 to 80 optionally from 40 to 75, optionally from 40 to 70, optionally from 45 to 65, optionally from 50 to 60 wt. %. In particular embodiments, the sunflower seed protein material comprises a protein content of from 60 to 80 wt. %. In certain embodiments the sunflower seed protein material comprises a protein content of from 80 to 90 wt. %. Methods for determining the protein content of the sunflower seen protein material are known in the art and include methods conventionally utilized for determining the protein content of compositions for foodstuffs, beverages, etc. Such methods typically comprise analytical procedures for measuring protein content by determining the nitrogen content/composition of a sample, and may include the Kjedahl method for nitrogen determination (also known as the Kjeldahl digestion method, Kjedahl nitrogen analysis, etc.), a combustion method (e.g. the Dumas method), and/or near infrared (NIR) analysis, as known by those of skill in the art.

In particular embodiments, the sunflower seed protein material comprises a concentrated sunflower seed meal comprising a $CO_2$ oil expressed sunflower seed concentrate having a protein content of approximately 55 wt. %, which has been processed by post-extraction ($CO_2$) stratification (e.g. with screens, air classification, etc.) to remove fiber and increase protein content in the resulting concentrated sunflower seed meal.

In some embodiments, the method of preparing the protein hydrolysate composition comprises combining the protein material and water (e.g. via dispersing, mixing, etc.) to form a slurry. In such embodiments, the slurry is not limited, and may be independently selected (e.g. in view of a desired pH, loading, temperature, etc.).

In certain embodiments, the slurry comprises the protein material in an amount of from 1 to 20% (w/v), such as from 1 to 15, optionally from 5 to 15, optionally of from 8 to 12% (w/v). In specific embodiments, the slurry comprises the protein material in an amount of about 10% (w/v). In some embodiments, the protein material is combined with water such that the slurry comprises a protein content of from 1 to 20% (w/v), such as from 1 to 15, optionally from 5 to 15, optionally of from 8 to 12, optionally of about 10% (w/v). However, it is to be appreciated that values outside of these ranges may also be utilized, as will be understood by those of skill in the art.

Once formed, the slurry may be heated and/or pH adjusted. The pH may be adjusted by any method, and generally includes adding an acid (e.g. HCl), a base (e.g. NaOH), a buffer, or combinations thereof, to the slurry. In general, the pH of the protein slurry may be adjusted and monitored by any means, which are generally known in the art. More specifically, the pH of the slurry is typically adjusted to a desired value, which may be selected based on desired reaction parameters (e.g. in view of slurry loading, volume, temperature, desired hydrolysis reagent(s), etc.). For example, the pH of the slurry may be adjusted to and/or maintained at from a pH of from 2 to 10, such as from 2 to 9, optionally of from 2 to 8, optionally of from 3 to 8, optionally of from 4 to 8, optionally of from 5 to 8, optionally of from 6 to 8, optionally of from 6 to 7. In certain embodiments, the pH of the slurry is adjusted to and/or maintained at from a pH of from 6.0 to 7.1, such as a pH of about 6.0, 6.1, 6.2, 6.3, 6.4, 6.5, 6.6, 6.7, 6.8, 6.9, 7.0, 7.1, or 7.2. In particular embodiments, the pH of the slurry is adjusted to and/or maintained at a pH of about 6.8. It is to be appreciated that values outside of these ranges may also be utilized, as will be understood by those of skill in the art in view of the description herein. For example, in particular embodiments, as described in further detail below, the protein material is enzymatically hydrolyzed. In such embodiments, the particular pH of the slurry will typically be adjusted to optimize the hydrolysis activity of enzymes utilized, and may also be varied to increase/decrease the rate of the hydrolysis reaction and/or to stop the hydrolysis reaction.

The temperature of the slurry may also be adjusted to and/or maintained at a desired temperature value (e.g. via heating, cooling, etc.) during any stage of the method (e.g. before, after, or during pH adjustment, hydrolysis, etc.). For example, the temperature of the slurry may be adjusted to a first/initial value, and subsequently to a second value, third value, etc., which may each be independently elevated or reduced with respect to one another. In some embodiments, the temperature of the slurry is adjusted to an initial value of from greater than room temperature to 85° C., such as a temperature of from greater than 25 to 85, optionally of from 35 to 85, optionally of from 45 to 85, optionally of from 55 to 85° C. before the pH of the slurry is adjusted. In these or other embodiments, the temperature of the slurry is adjusted to an initial value of from greater than room temperature to 60° C., such as a temperature of from greater than 25 to 60, optionally of from 35 to 60, optionally of from 45 to 60, optionally of from 50 to 60, optionally of from 55 to 60° C. In certain embodiments, the slurry is heated to an initial temperature of greater than 70, optionally greater than 80, optionally greater than 90° C., and held at that initial temperature for a time sufficient to inactivate endogenous protease inhibitors in the protein material (e.g. via denaturation).

As introduced above, the method of preparing the protein hydrolysate composition comprises hydrolyzing the protein material to give the isolated peptides of SEQ ID NO: 1, SEQ ID NO: 2, SEQ ID NO: 3, and SEQ ID NO: 4. The hydrolysis of the protein material typically comprises enzymatic hydrolysis (i.e., hydrolytic proteolysis), although other hydrolysis techniques (e.g. fermentation, acid/base hydrolysis, etc.) may also be utilized. It is to be appreciated that the term "isolated" as defined above, with respect to the isolated peptides of SEQ ID NO: 1, SEQ ID NO: 2, SEQ ID NO: 3, and SEQ ID NO: 4, is satisfied by and/or includes hydrolysis as a method of separating naturally occurring peptide sequences from their natural/original environment, and in this case also transforming those peptide sequences into individual peptides.

In various embodiments, hydrolyzing the protein material includes combining the protein material (e.g. in the slurry) and a composition comprising a protease (the "protease composition") to give a reaction mixture. The protease composition is not particularly limited, and comprise any number of endopeptidases, exopeptidases, or combinations thereof, which are capable of facilitating the proteolysis of proteins and/or peptides in the protein material to give peptides of SEQ ID NO: 1, SEQ ID NO: 2, SEQ ID NO: 3, and SEQ ID NO: 4. In certain embodiments, the protease composition is a food-grade composition, as will be appreciated in view of the compositions described herein.

The particular proteases (also known as hydrolytic enzymes, peptidases, etc.) of the protease composition may vary, but are typically selected from those exhibiting activity under the conditions described above, as described in further detail below. General examples of proteases include serine proteases, aspartic acid proteases, cysteine proteases, metalloproteases, threonine proteases, glutamic acid proteases, aminopeptidases, dipeptidyl peptidases, ungrouped proteases, and combinations thereof. Some specific examples of endopeptidases include pepsin, thermolysin, trypsin, chymotrypsin, pancreatin, and combinations thereof. Other particular proteases, which may be provided or otherwise utilized as isolated/purified enzymes or enzyme compositions, include alkaline serine endopeptidases, metallo neutral endopeptidases, acid fungal endopeptidases, bacterial alkaline serine endopeptidases, subtilisins, acid fungal endo/exopeptidase complexes, neutral fungal endo/exopeptidase complexes, thermolysin-enzyme complexes, aspergillopepsin I-enzyme complexes, bacillolysin-enzyme complexes, oryzin-enzyme complexes, rhizopupepsin-enzyme complexes, compounded protease preparations (e.g. naturally and/or synthetically derived), and the like, as well as derivatives, modifications, and combinations thereof.

In certain embodiments, the protease composition comprises, optionally is, Flavourzyme, which is a compounded protease possessing endopeptidase and exopeptidase activity and was identified from *Aspergillus oryzae* by Novo Nordisk Company.

The amount of protease combined with the protein material may vary, e.g. based on the source of the protein material, the desired degree of hydrolysis, the particular protease composition selected, the hydrolysis conditions utilized, the duration of the hydrolysis reaction, etc. Typically, the amount of protease combined with the protein material is from 1 to 100 g of enzyme protein per kilogram of protein material (i.e., from 0.1 to 10% w/w protein). In certain embodiments, the amount of protease combined with the protein material is from 5 to 90, optionally from 10 to 90, optionally from 10 to 80, optionally from 20 to 80, optionally from 20 to 70, optionally from 20 to 60, optionally from 30 to 50 g of enzyme protein per kilogram of protein material (w/w). However, it is to be appreciated that amounts outside of these ranges/values may also be utilized (e.g. depending on the particular components and conditions selected), as will be understood by those of skill in the art in view of the description herein.

As introduced above, the particular protease(s) of the protease composition is/are typically selected from those exhibiting activity under the conditions described above regarding the pH and/or temperature of the slurry. However, one of skill in the art will appreciate that the pH and/or temperature of the slurry will typically be selected to optimize the hydrolytic activity of the proteolytic enzymes of the protease composition. As such, in addition to the conditions described above, the method may include adjusting the pH and/or temperature of the slurry to within an optimal activity range of the protease composition. For example, the method may include combining the protease composition and the slurry at the initial temperature, where the initial temperature is selected to optimize the proteolytic activity of the protease composition. In certain embodiments, the method includes heating the slurry to the initial temperature of greater than 80° C. prior to combination of the protease composition, and subsequently reducing the temperature of the slurry to the value of from greater than room temperature to 60° C. and maintaining that temperature value for the duration of the hydrolysis.

The duration of the hydrolysis is not limited, and is typically selected, e.g. based on the particular protease composition, protein material, slurry formulation, pH, temperature, etc., and the like, or combinations thereof. In certain embodiments, the duration of the hydrolysis may range from a few minutes to many hours, such as from 5 minutes to 48 hours. However, the components and conditions of the hydrolysis reaction are typically selected to facilitate hydrolysis during a duration of from 30 minutes to 10 hours, such as from 1 to 9, optionally from 2 to 8, optionally from 2 to 7, optionally from 3 to 7, optionally from 3 to 6, optionally from 3 to 5 hours. In certain embodiments, the duration is about 3, 4, or 5 hours. However, it is to be appreciated that durations outside of these ranges/values may also be utilized, as will be understood by those of skill in the art in view of the description herein.

In certain embodiments, the method includes stopping the hydrolysis reaction once hydrolysis of the protein material is deemed complete (i.e., the selected duration of the hydrolysis has expired) and a reaction product comprising the isolated peptides of SEQ ID NO: 1, SEQ ID NO: 2, SEQ ID NO: 3, and SEQ ID NO: 4 has been thereby prepared. In such embodiments, stopping the hydrolysis reaction typically comprises adjusting the temperature of the reaction mixture to a temperature greater than 80, optionally greater than 85, optionally greater than 90, optionally greater than 95° C., and holding the reaction mixture at that temperature for a time sufficient to inactivate the protease(s) present therein, thereby giving the reaction product comprising the isolated peptides. In these or other embodiments, stopping the hydrolysis reaction comprises adjusting the pH of the reaction mixture to a pH outside (e.g. above or below) the operating range of the protease(s) present therein. For example, in some embodiments, the method includes stopping the hydrolysis reaction by adding an acid to the reaction mixture. Regardless of the particular technique selected to stop the hydrolysis reaction, the activity or inactivity of the protease(s) may be monitored and/or confirmed by various methods known in the art, such as via protease activity assays, kits, test strips, and the like, or combinations thereof.

In certain embodiments, the reaction product of the hydrolysis reaction is further defined as a crude reaction product comprising the isolated peptides, and the method further comprises purifying the crude reaction product to give a purified reaction product comprising peptides of SEQ ID NO: 1, SEQ ID NO: 2, SEQ ID NO: 3, and SEQ ID NO: 4. In general, purifying the crude reaction product comprises increasing the overall concentration of any or all of the peptides of SEQ ID NO: 1, SEQ ID NO: 2, SEQ ID NO: 3, and SEQ ID NO: 4 in relation to one or more other components combined therewith (e.g. other peptides, biological materials, fats, fibers, oils, carriers, solvents, etc.).

Purifying the crude reaction product may comprise any method(s) known in the art, including filtration, phase separation (e.g. based on solubility, freeze point, etc.), centrifugation, chromatographic methods such as size exclusion chromatography, ion exchange chromatography, affinity chromatography, hydrophobic interaction chromatography, reverse phase chromatography, etc., and the like, as well as variations and combinations thereof. In some embodiments, purifying the crude reaction product comprises centrifugation to give the purified reaction product as a soluble supernatant, which is then fractionated via preparative reverse-phase high-pressure liquid chromatography (HPLC) to give a fraction comprising isolated peptides of SEQ ID NO: 1, SEQ ID NO: 2, SEQ ID NO: 3, and SEQ ID NO: 4. In such embodiments, the fraction comprising the isolated peptides of SEQ ID NO: 1, SEQ ID NO: 2, SEQ ID NO: 3, and SEQ ID NO: 4 may be, optionally may be used in (e.g. via compounding, formulating, etc.), the protein hydrolysate composition.

In general, the protein hydrolysate composition is not limited in terms of formulation, peripheral ingredients, form, number of functions, etc., aside from comprising the isolated peptides of SEQ ID NO: 1, SEQ ID NO: 2, SEQ ID NO: 3, and SEQ ID NO: 4, which may be utilized as and/or provided from the reaction product, crude reaction product, and/or purified reaction product described above. Rather, the protein hydrolysate composition may be varied, and may be formulated in any fashion consistent with this disclosure.

As described below, the protein hydrolysate composition may be utilized to ameliorating a condition of and/or confer a health benefit to a subject. As such, in certain embodiments, the composition comprises an active agent. Typically, the active agent comprises, optionally is, the isolated peptides. However, in various embodiments, the composition comprises multiple active agents, which may each be independently selected. In such embodiments, at least one of the active agents comprises, optionally is, the isolated peptides described above. However, other active agents (e.g. probiotics, prebiotics, parabiotics, pharmaceuticals, nutraceuticals, anesthetics, counterirritants, chondroprotective agents, etc.) may be utilized in addition to the isolated peptides. For example, in certain embodiments, the protein hydrolysate composition comprises a pharmaceutical agent, such as an angiotensin converting enzyme (ACE) inhibitor, an anti-inflammatory medication, a vasodilator, an immune modulating agent (e.g. an antibody therapeutic agent), an analgesic, an antibiotic, or the like, or a combination thereof.

In particular embodiments, the protein hydrolysate composition comprises a combination of the isolated peptides and the additional active agent. In specific embodiments, the protein hydrolysate composition is provided as a kit, where the kit includes a first component comprising the isolated peptides and a second component comprising the additional active agent. In some such embodiments, the additional active agent is a pharmaceutical agent, thus as those described herein. The components of the kit may be administered together or separately (e.g. sequentially, in any order).

In addition to the active agent, the protein hydrolysate composition may comprise any number of additional ingredients/components. For example, in some embodiments, the protein hydrolysate composition comprises an additive component, which may comprise one or more additives. Examples of suitable additives for use in the additive component include amino acids, peptides, proteins, lipids, vitamins, carbohydrates, nucleic acids, minerals, anabolic nutrients, antioxidants, probiotic bacterial strains, lipotropic agents, extracts, concentrates, oils, gums, and combinations thereof. In certain embodiments, the additive component comprises a flavoring agent, a dye, a flow modifier, a preservative, a filler, a binder, a dispersing agent, a carrier, a supplemental nutrient, or any combination thereof. In particular embodiments, the additive component comprises a carrier, such as a consumable, nutritional, and/or pharmaceutical carrier, or a combination thereof. Of course, components aside from the additive component may also be utilized in the protein hydrolysate composition. For example, the protein hydrolysate composition may comprise a fat component, a lipid component, a protein component, a fiber component, a carbohydrate component, and the like, or combinations thereof, which may be independently selected, e.g. based on the desired formulation, form, and/or end use of the protein hydrolysate composition, as will be understood by those of skill in the art in view of the description herein.

In certain embodiments, the protein hydrolysate composition comprises a vehicle (i.e., a carrier vehicle, carrier, etc.) that may be independently selected (e.g. based on the desired formulation, form, and/or end use of the protein hydrolysate composition, etc.). Suitable vehicles and vehicle components are well known in the supplement, cosmetic, and pharmaceutical arts, and include water (e.g. purified, deionized, etc.); organic solvents such as alcohols (particularly lower alcohols readily capable of evaporating from the skin such as ethanol), glycols (such as propylene glycol, pentylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids, and waxes; protein-based materials such as collagen and gelatin; silicone-based materials (both non-volatile and volatile) such as cyclomethicone, dimethiconol, and dimethicone copolyol; hydrocarbon-based materials such as petrolatum, hydrogenated polyisobutene, and squalane; emollient esters (such as diisobutyl adipate and caprylates), thickening agents (acrylates (carbomers), acrylamides, acryl taurates, hydroxyethylcellulose, methyl cellulose, xanthan gum, etc.), and the like, as well as derivatives, modifications, and combinations thereof.

Certain embodiments of the protein hydrolysate composition, which vary in terms of formulation and/or form, are described below. However, as introduced above, the protein hydrolysate composition is not particularly limited with regard to substance and/or function, and may comprise any number of components/ingredients in addition to the isolated peptides, such as the active agents and/or additives described above. In general, the components of the protein hydrolysate composition will be individually or collectively selected based on an intended use of the protein hydrolysate composition, as will be readily understood by those of skill in the art. Typically, the protein hydrolysate composition is formulated or otherwise adapted for administration to a mammal (e.g. a human). For example, in various embodiments, the protein hydrolysate composition is adapted to be consumed and/or topically administered. As such, the particular additives, carriers, adjuvants, fillers, etc. present in or combined with the protein hydrolysate composition may vary. Moreover, the physical form of the protein hydrolysate composition is not limited. Rather, as will be understood in view of the description herein, the protein hydrolysate composition may be formulated as a liquid, dry powder, suspension, emulsion, gel, paste, etc., and combinations thereof.

In some embodiments, the protein hydrolysate composition is formulated or otherwise adapted for consumption (e.g. by an animal). In such embodiments, the protein hydrolysate composition may be adapted to be consumed as a liquid or a powder, and thus may compose, optionally may be further defined as, a foodstuff or beverage.

For example, in certain embodiments, the protein hydrolysate composition is adapted to be mixed with a foodstuff or beverage. The term "foodstuff" is used herein to refer to a material that may be used as a food. As such, in certain instances the term foodstuff is used to describe a composition that may be consumed (e.g. by eating) by a living organism (e.g. a mammal), for nourishment and/or sustenance. Likewise, the term "beverage" as used herein refers to a potable liquid or other non-solid composition. However, in certain instances, the term beverage is used to describe a non-solid (e.g. liquid, slurry, suspension, etc.) composition that may be consumed by a living organism for nourishment and/or sustenance. As such, in particular instances the terms "beverage" and "foodstuff" may overlap. In certain instances, the term "nutritional composition" is used to describe a foodstuff and/or beverage formulation that can be eaten or drunk by a human subject for nutrition. Accordingly, in some embodiments, the protein hydrolysate composition is, optionally is a component of, a foodstuff or beverage.

In these or other embodiments, the protein hydrolysate composition may be further defined as a food additive. As used herein, the term "food additive" refers to an ingredient, additive, component, or supplement suitable for incorporation in a foodstuff and/or beverage to confer a technical, nutritional, and/or health benefit (i.e., a function) to a host that consumes the foodstuff and/or beverage. Accordingly, such benefits may be closely related to the presence of the isolated peptides of SEQ ID NO: 1, SEQ ID NO: 2, SEQ ID NO: 3, and SEQ ID NO: 4 in the protein hydrolysate composition. The food additive can be added to different types of food including, but not limited to, medical foods, dietetic foods, and supplements. Certain aspects of the present embodiments can include the use of the protein hydrolysate composition as a food additive, and the use of the protein hydrolysate composition in methods of preparing foodstuffs and/or beverages.

In general, when utilized as a component of a foodstuff or beverage, the foodstuff or beverage comprises an admixture of the protein hydrolysate composition with one or more feed products, liquids, supplements, or combinations thereof. However, in certain embodiments, the protein hydrolysate composition may itself be further defined as a foodstuff or beverage composition, depending on the quantity, nature, and identity of individual additives and components present in the composition, such as those described herein. Thus, it is to be appreciated that the embodiments described herein with respect to the protein hydrolysate composition in general may equally encompass the foodstuff or beverage, a food or beverage product, and/or a food supplement comprising the protein hydrolysate composition. Accordingly, any amounts and/or examples of such components (e.g. in addition to the isolated peptides) described herein with respect to the protein hydrolysate composition itself may equally apply to the foodstuff or beverage comprising the protein hydrolysate composition, as will be understood by one of skill in the art.

In some embodiments, the foodstuff or beverage comprising the protein hydrolysate composition is further defined as a nutritional composition. In these or other embodiments, the nutritional composition is in the form of a dry food concentrate, which may be mixed with liquid or food and subsequently consumed.

In some embodiments, the foodstuff or beverage comprising the protein hydrolysate composition is further defined as a medical food. In such embodiments, the medical food comprises the protein hydrolysate composition, and may be the same as or different from the nutritional composition described above. As used herein, the term "medical food" is typically used to refer to a food for a special dietary use, such as a food formulated for dietary management of a medical condition (e.g. based upon scientific or medical evaluation). However, it is to be appreciated that the term "medical food" may have one or more particular definitions depending on, for example, geographic location, specific use, regulatory agency, and the like. For example, in certain cases, the term medical food may be defined as a food which is formulated to be consumed or administered enterally under the supervision of a physician and which is intended for the specific dietary management of a disease or condition for which distinctive nutritional requirements, based on recognized scientific principles, are established by medical evaluation (see, e.g. section 5(b) of the Orphan Drug Act (21 U.S.C. 360ee (b) (3)), which is incorporated herein by reference). In these or other instances, the term medical food may be defined as a food for special dietary use as a food that has been specially processed or formulated to meet the particular requirements of a person: (a) in whom a physical or physiological condition exists as a result of a disease, disorder, or injury; or (b) for whom a particular effect, including but not limited to weight loss, is to be obtained by a controlled intake of food (see, e.g. section B.24.001 of the Canadian Food and Drug Regulations (FDR, C.R.C., c. 870) (as amended 13 Jun. 2017)), which is incorporated herein by reference).

In certain embodiments, the protein hydrolysate composition may be further defined as a nutritional supplement, or as a complete nutritive. As used herein, the term "supplement" relates to a nutritional supplement which is a concentrated source of nutrient or optionally other substances with a nutritional or physiological effect whose purpose is to supplement the normal diet. For example, the protein hydrolysate composition may be formulated to provide a mammal (e.g. a human), via consumption of the protein hydrolysate composition, with at least 1%, optionally at least 2%, optionally at least 5%, optionally at least 10%, optionally at least 25%, optionally at least 50%, of daily calories required by the mammal. In particular embodiments, the protein hydrolysate composition may be formulated to provide the mammal, via consumption of the protein hydrolysate composition, with 0.1 to 15, optionally from 0.2 to 10% of daily calories required by the mammal. However, it is to be appreciated that a daily calorie requirement is dependent on several factors, including the gender, height, and/or age of the mammal, and thus the percentage of caloric requirement provided by the protein hydrolysate composition will be dependent on the particular person consuming the nutritional composition composed therefrom. For example, a 30 year old human male of 80 kg body weight and 180 cm height has a daily calorie requirement of around 2900 cal (calories) to maintain his body weight whereas a 30 year old human female of 55 kg body weight and 165 cm height has a daily calorie requirement of around 2100 cal to maintain her body weight. Moreover, daily caloric requirements may be reduced from the amount required to maintain body weight, e.g. where the mammal is intentionally reducing body weight.

It is to be appreciated that the protein hydrolysate composition, e.g. itself and/or when formulated as described in any of the embodiments above (e.g. as the nutritional composition) is distinguished from a vaccine. In particular, each of the various compositions described herein may be free from, optionally substantially free from, a vaccine.

In certain embodiments, the protein hydrolysate composition is further defined as an animal food. In such embodiments, the protein hydrolysate composition is typically formulated for ingestion by one or more non-human animals, such as livestock including cattle, swine, horses, sheep, goats, poultry, and fish, domesticated companionship species such as dogs, cats, fish, and rodents, undomesticated wildlife such as deer, moose, elk, migratory, and non-migratory fowl, those non-human animals described herein, and combinations thereof. In certain instances, administering the protein hydrolysate composition as the animal food to a non-human subject (e.g. an animal) may result in an increased yield in one or more commodities produced by the host, such as eggs, meat, milk, wool, etc.

In some embodiments, the protein hydrolysate composition is formulated or otherwise adapted for topical or transdermal administration, and thus may compose, optionally may be further defined as, a topical composition. In such embodiments, the topical composition comprising the protein hydrolysate composition (herein referred to as the "topical composition" for brevity), is typically formulated to provide the isolated peptides to a part of a subject via direct application (e.g. topically to surfaces such as skin, mucous membranes, etc.) and/or indirect application (e.g. transdermally to internal tissues via transport/migration/absorption through skin, mucous membranes, etc.). The particular formulation of the topical composition is not limited and may vary, as will be understood in view of the description below. As such, the amount of any particular component may be individually selected, e.g. based a desired end form (e.g. cream vs. spray, etc.), as readily understood by those of skill in the art. Additionally, the topical composition and may comprise any form for topical or transdermal administration, including powders, sprays, ointments, pastes, creams, lotions, gels, solutions, patches, inhalants, and the like, as well as combinations thereof.

As introduced above with regard to the protein hydrolysate composition, in addition to the isolated peptides the topical composition may comprise an additional active agent and/or additives, such as one or more of those described above. The topical composition may comprise other additives selected specifically for use in formulating and/or using the topical composition. For example, in certain embodiments, the topical composition also comprises a pharmaceutically/medically acceptable carrier, a functional additive, a formulation additive, or a combination of such additives, e.g. selected based on a desired form of the topical composition, use of the topical composition, etc.

In some embodiments, the topical composition comprises the pharmaceutically acceptable carrier. As understood by those of skill in the art, the carrier is typically selected to be generally compatible with the individual components of the topical composition and to enhance, or to not interfere significantly with, the transport of the isolated peptides, and optionally other components of the topical composition, through a subject's skin. Accordingly, general examples of suitable carriers include those that promote, facilitate, and/or tolerate transport of the isolated peptides, and optionally other components of the topical composition, through skin. Particular examples of such carriers include water (e.g. deionized), oils and/or waxes (e.g. mineral oils, synthetic oils, natural oils such as jojoba oil, castor oil, etc., and waxes formed therewith), alcohols (e.g. monols, diols, and polyols such as ethanol, isopropanol, butanediol, 1,2,6-hexanetriol etc., glycols such as ethylene glycol, propylene glycol, etc.), polyoxyalkylenes and/or polyoxyalkylene esters (e.g. polyethylene glycols, polypropylene glycols, mixed polyalkylene glycols, polyethylene glycol-8 stearates, etc.), fatty acid esters (e.g. alkyl stearates, oleates, linoleates, isopropyl palmitate, etc.), organic polymers (e.g. polyacrylamides), organic solvents (e.g. dimethylsulfoxide, dimethylformamide, dimethylacetamide, methylsulfonylmethane), and the like, as well as derivatives, modifications, and combinations thereof, and any of the other carriers described herein, such as applicable vehicle and/or vehicle components described above.

In particular embodiments, the topical composition comprises the functional additive. The functional additive is not limited, and may comprise, optionally may be, any compound or composition selected to provide a functional characteristic to, or impart a function on, the topical composition. Examples of such functional additives include anti-oxidants (e.g. alkylates hydroxytoluenes, hydroxyanisoles, etc., propyl gallate, etc.), colorants, moisturizers and emollients (e.g. sunflower oil, jojoba oil, isopropyl palmitate, etc.), perfumes (e.g. natural perfumants such as rosemary oil, synthetic perfumes, etc.), cooling agents (e.g. peppermint oil), preservatives (e.g. antimicrobial and antifungal agents, such as propylene glycol, methyl paraben, propyl paraben, diazodinyl urea, etc.), and the like, as well as derivatives, modifications, and combinations thereof.

For example, in certain embodiments, the topical composition comprises a moisturizer. Examples of suitable moisturizers include hydroxy acids (e.g. lactic acid) and their salts, glycerol, propylene glycol, pentylene glycol, butylene glycol, sodium salts of pyrrolidone carbonic acid (i.e., sodium PCA), sodium hyaluronate, polyethylene glycols (PEG) (e.g. CARBOWAX PEG 200, CARBOWAX PEG 400, CARBOWAX PEG 800, etc.), and the like, as well as derivatives, modifications, and combinations thereof. In these or other embodiments, the topical composition comprises an emollient and/or a humectant. Examples of suitable emollients or humectants include cetyl palmitate, glycerol (i.e., glycerin), polypropylene glycol-15 stearyl ether (i.e., PPG-15 stearyl ether), lanolin and derivatives thereof (e.g. lanolin alcohol, etc.), cholesterol, petrolatum, isostearyl neopentanoate, octyl stearate, mineral oil, isocetyl stearate, myristyl myristate, octyl dodecanol, octyl palmitates (e.g. 2-ethylhexyl palmitate), dimethicone, phenyl trimethicone, cyclomethicone, $C_{12}$-$C_{15}$ alkyl benzoates, dimethiconol, propylene glycols, pentylene glycols, *Theobroma grandiflorum* seed butter, shea butter, ceramides (e.g. ceramide 2, ceramide 3, etc.), hydroxypropyl bispalmitamide MEA, hydroxypropyl bislauramide MEA, hydroxypropyl bisisostearamide MEA, 1,3-bis-(N-2-(hydroxyethyl) stearoylamino)-2-hydroxy propane, bis-hydroxyethyl tocopherylsuccinoylamido hydroxypropane, urea, aloe, allantoin, glycyrrhetinic acid, dicaprylate/dicaprates, and the like, as well as derivatives, modifications, and combinations thereof.

In certain embodiments, the topical composition comprises a preservative. Examples of suitable preservatives include ureas (e.g. imidazolidinyl urea, diazolidinyl urea, etc.), phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, quaternary ammonium preservative compounds (e.g. benzalkonium chloride, benzethonium chloride, cetrimide, dequalinium chloride, cetylpyridinium chloride, etc.), mercurial preservative agents (e.g. phenylmercuric nitrate, phenylmercuric acetate, thimerosal, etc.), piroctone olamine, *Vitis vinifera* seed oil, alcoholic preservative agents (e.g. chlorobutanol, dichlorobenzyl alcohol, phenylethyl alcohol, benzyl alcohol, etc.), and the like, as well as derivatives, modifications, and combinations thereof. In these or other embodiments, the topical composition comprises an antioxidant. Examples of suitable antioxidants include ascorbic acid and esters thereof, sodium bisulfite, butylated hydroxytoluene, butylated hydroxyanisole, tocopherols (e.g. α-tocopherol), tocopheryl acetate, sodium ascorbate/ascorbic acid, ascorbyl palmitate, ascorbyl glucoside, propyl gallate, chelating antioxidants (e.g. ethylenediaminetetraacetic acid (EDTA), disodium EDTA, etc.), citric acid, sodium citrate, and the like, as well as derivatives, modifications, and combinations thereof.

In certain embodiments, the topical composition comprises the formulation additive. The formulation additive is not limited, and may comprise, optionally may be, any compound or composition selected to impart a physical characteristic to the topical composition. Examples of such formulation additives include emulsifiers (e.g. isoparaffins such as $C_{13}$-$C_{14}$ isoparaffin, surfactants such as laureth-7, polymers such as polyacrylamides and polyalkyleneglycols, etc.), buffers, excipients, propellants, and the like, and combinations thereof. Typically, the formulation additive is selected based on the desired form of the topical composition. For example, in some embodiments, the topical composition is formulated as an ointment, paste, cream, and/or gel, and comprises an excipient exemplified by animal and vegetable fats, oils, waxes, paraffins, starch, tragacanth, cellulose derivatives, polyethylene glycols, silicones, bentonites, silicic acid, talc, zinc oxide, and the like, as well as derivatives, modifications, and combinations thereof. In certain embodiments, the topical composition is formulated as a powder and/or spray, and comprises an excipient exemplified by lactose, talc, silicic acid, aluminum hydroxide, calcium silicates, polyamide powders, and the like, as well as derivatives, modifications, and combinations thereof. In particular embodiments, the topical composition is formulated as a spray and a propellant, such as a volatile organic compound exemplified by halogenated hydrocarbons (e.g. hydrocarbons substituted with chlorine, fluorine, or both) and low molecular weight unsubstituted hydrocarbons (e.g. butane, propane, etc.). In general, the topical composition comprises the formulation additive in an amount of from 1.0 to 20.0 wt. %, based on the weight of the topical composition.

In particular embodiments, the topical composition comprises a lipophilic solubilizer. Some examples of lipophilic solubilizers include non-comedogenic esters, such as adipates (e.g. diisobutyl adipate), caprylates, isononanoates (e.g. isononyl neopentanoate), ethoxylated triglycerides, and the like, as well as modifications, derivatives, and combinations thereof. Other examples of lipophilic solubilizers generally include cetyl esters, polyethylene glycol cetyl esters, hydrogenated polyisobutenes, argan oil, soybean oil, chemical UV filters/boosters (e.g. octisalate, octinoxate, butyl octyl salicylate, etc.), and the like, as well as modifications, derivatives, and combinations thereof.

In some embodiments, the topical composition comprises a free radical stabilizer. Examples of free radical stabilizers generally include lipophilic antioxidants, such as tocotrienolss, carotenoids (e.g. tocopherol, tocopherol acetate, retinyl palmitate, tetrahexydecyl ascorbate, lutein, natural oils rich in unsaturated fatty acids such as docosahexaenoic acid, etc.), and the like, as well as modifications, derivatives, and combinations thereof.

In certain embodiments, the topical composition comprises a surfactant. Examples of suitable surfactants include ionic (e.g. anionic, zwitterionic, etc.) and non-ionic surfactants. Some specific examples of such surfactants include polysorbates (e.g. polyoxyethylene (20) sorbitan monolaurate (i.e., Polysorbate 20), polyoxyethylene (20) sorbitan monopalmitate (i.e., Polysorbate 40), polyoxyethylene (20) sorbitan monostearate (i.e., Polysorbate 60), polyoxyethylene (20) sorbitan monooleate (i.e., Polysorbate 80), etc.), vegetable sorbitan stearates, steareth-10 and other octadecyl polyoxyethylene ethers, sodium dodecyl sulfates (e.g. sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (e.g. sodium deoxycholate, sodium cholate, etc.), polyoxyl castor oil, nonylphenol ethoxylate, cyclodextrins, lecithin, dimethicone copolyol, lauramide diethanolamine, cocamide diethanolamine, cocamide monoethanolamine, betaines (e.g. oleyl betaine, cocamidopropyl betaine, etc.), cocamidopropyl phosphatidyl PG-dimonium chloride, dicetyl phosphate (dihexadecyl phosphate), ceteareth-10 phosphate, polyglyceryl-2 triisostearate, cetyl PEG/PPG-1/1 dimethicone (ethoxylated or organo-modified silicones for W-in-Si emulsions, glyceryl stearate, glyceryl dilaurate, lecithin, unsaturated lecithin, etc.), methylbenzethonium chloride, and the like, as well as modifications, derivatives, and combinations thereof.

In some embodiments, the topical composition comprises an emulsifier, which may be the same as or different from the surfactant. Examples of such emulsifiers include behentrimonium methosulfate-cetearyl alcohol, non-ionic emulsifiers (e.g. emulsifying waxes), polyoxyethylene oleyl ethers, polyethylene glycol stearates (i.e., PEG-40 stearate, PEG-100 stearate, etc.), cetostearyl alcohols (e.g. cetearyl alcohol), ceteareth-12, ceteareth-20, ceteareth-30, ceteareth alcohol, glyceryl stearate, steareth-2 and steareth-20, cationic emulsifiers (e.g. stearamidopropyl dimethylamine, behentrimonium methosulfate, etc.), and the like, as well as modifications, derivatives, and combinations thereof.

In particular embodiments, the topical composition comprises a viscosity adjusting agent (e.g. a thickening or thinning agent, which may be referred to as a viscosity modifier). Examples of such agents generally include protective colloids, non-ionic gums such as hydroxyethylcellulose, xanthan gum, and sclerotium gum, magnesium aluminum silicate, silica, microcrystalline waxes, beeswax, paraffin, cetyl palmitate, and the like, as well as modifications, derivatives, and combinations thereof.

In certain embodiments, the topical composition comprises one or more additional components, which may comprise or be selected skin protectants, adsorbents, demulcents, emollients, moisturizers, buffering agents, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g. witch hazel, alcohol, chamomile extract, etc.), binders/excipients, buffering agents, chelating agents, film forming agents, conditioning agents, opacifying agents, lipids, pH adjusters (e.g. citric acid, sodium hydroxide, sodium phosphate monobasic, sodium phosphate dibasic, etc.), and the like, as well as modifications, derivatives, and combinations thereof. Specific examples of such additional components are exemplified in U.S. Patent Application Publication No. 2018/0110722 A1, the disclosure of which regarding topical composition components is incorporated by reference herein.

Regardless of the particular form and/or formulation, including each of the compositions and forms described relative to the embodiments above, the protein hydrolysate composition typically comprises the isolated peptides in an amount sufficient to provide from 10 mg to 100 g of the isolated peptides (e.g. per dose and/or serving, or in total). For example, in certain embodiments, the protein hydrolysate composition is formulated to provide the isolated peptides in an amount of from 10 mg to 1 g per dose, such as from 10 to 750, optionally from 10 to 500, optionally from 20 to 500, optionally from 30 to 500, optionally from 50 to 500, optionally from 50 to 250, optionally from 50 to 100 mg, per dose of the protein hydrolysate composition. In particular embodiments, the protein hydrolysate composition is formulated to provide the isolated peptides in an amount of from 10 mg to 10 g per dose, such as from 20 mg to 10 g, optionally from 20 mg to 9 g, optionally from 20 mg to 8 g, optionally from 30 mg to 8 g, optionally from 40 mg to 8 g, optionally from 50 mg to 8 g, optionally from 50 mg to 7 g, optionally from 50 mg to 6 g, optionally from 50 mg to 5 g, per dose of the protein hydrolysate composition. In some embodiments, the protein hydrolysate composition is formulated to provide the isolated peptides in an amount of from 1 to 100 g per dose, such as from 1 to 50, optionally from 1 to 40, optionally from 1 to 30, optionally from 1 to 25, optionally from 1 to 20, optionally from 1 to 15, optionally from 1 to 10, optionally from 1 to 5 g, per dose of the protein hydrolysate composition. In such embodiments, the dose may be a single dose or, optionally, may be defined as a daily dose.

It is to be appreciated that the protein hydrolysate composition may comprise multiple doses of the isolated peptides, such as in the amounts described above, and thus may comprise any amount of the isolated peptides in total (e.g. such as an amount greater than 500 g, optionally greater than 1, 2, 5, 10, 50, 100, 500, or even 1000 kg). Likewise, as described above, the protein hydrolysate composition may comprise components other than the isolated peptides. As such, it will be appreciated that the protein hydrolysate composition may comprise the isolated peptides in various concentrations, such as from 0.001 to 99 wt. % based on the total dry weight of the protein hydrolysate composition (i.e., wt/wt). For example, in particular embodiments, the protein hydrolysate composition comprises the isolated peptides in an amount of from 1 to 98, optionally from 1 to 95, optionally from 1 to 90, optionally from 1 to 80, optionally from 1 to 70, optionally from 1 to 60, optionally from 1 to 50, optionally from 5 to 50, optionally from 10 to 50, optionally from 20 to 50 wt. % based on the total dry weight of the protein hydrolysate composition. In certain embodiments, the protein hydrolysate composition comprises the isolated peptides in an amount of from 0.001 to 10, optionally from 0.001 to 7.5, optionally from 0.001 to 5, optionally from 0.001 to 2.5, optionally from 0.001 to 1, optionally from 0.005 to 1, optionally from 0.01 to 1 wt. % based on the total dry weight of the protein hydrolysate composition.

As described and demonstrated by the Examples herein, the protein hydrolysate composition of this disclosure exhibits biological activity, including antioxidant and anti-inflammatory activities, which are mediated by the isolated peptides contained therein. As described below, this biological activity may advantageously be used in and/or by a subject. In certain embodiments, the antioxidant and/or anti-inflammatory activity of the isolated peptides produced by the methods herein may be significantly greater than the antioxidant and/or anti-inflammatory activity of either the native proteins and/or peptides in the protein material (e.g. sunflower seed protein), or such protein subjected to a conventional hydrolysis. In these embodiments, the antioxidant and/or anti-inflammatory activities, among others, may be quantified using different methods, such as a NFκB-Luciferase Reporter Gene Assay, a Co-Stimulatory Molecule Expression (Cluster Of Differentiation (CD)) Assay, a Nuclear Factor (Erythroid-Derived 2)-Like 2 (NRF-2) Assay, a Quinone Reductase (QR) Assay, a 2,2-Diphenyl-1-Picryl-Hydrazyl-Hydrate (DPPH) Assay, a Hydroxyl Radical Scavenging Activity (HRSA) Assay, a Nitric Oxide (NO) Production Assay, an Angiotensin-Converting Enzyme (ACE) Inhibition Assay, a Renin Inhibition Assay, and the like, and combinations thereof. These assays may be performed according to methods known in the art, and are exemplified by particular methods set forth in the Examples herein.

As described above, the protein hydrolysate composition may be formulated in various ways to facilitate administration of the same to a subject (e.g. via consumption, topical application, etc.). More specifically, the isolated peptides of the protein hydrolysate composition may be administered to the subject to confer a benefit thereto, as described in further detail below. Accordingly, a method of utilizing the protein hydrolysate composition (the "treatment method") is provided, and is useful in ameliorating a condition of the subject. In general, the treatment method comprises administering the protein hydrolysate composition to the subject.

The protein hydrolysate composition may provide or mediate a particular therapeutic and/or prophylactic effect, and thus may be used (e.g. according to the treatment method) to treat or ameliorate a condition in a subject. As used herein, the term "treat" refers to an approach for obtaining beneficial or desired results including a therapeutic benefit and/or a prophylactic benefit. A therapeutic benefit can be partial or complete eradication or amelioration of an underlying disorder being treated, whether temporarily or permanently. As such, a therapeutic benefit can be achieved with the eradication or amelioration of one or more physiological symptoms associated with the underlying disorder, such that an improvement is observed in the subject, notwithstanding that the subject may still be afflicted with the underlying disorder. A prophylactic effect includes delaying, preventing, and/or eliminating the onset and/or appearance of a disease or condition, slowing, halting, and/or reversing the progression of a disease or condition, or combinations thereof. As such, any of these effects may be a prophylactic benefit, and may be achieved in a subject at risk of developing a particular disease. Accordingly, a subject reporting one or more physiological symptoms of a disease may undergo treatment (e.g. with the protein hydrolysate composition), even in the absence of a diagnosis of the disease.

The treatment method may be used to ameliorate conditions introduced above, i.e., by mediating a biological effect in the subject. For example, the treatment method may be used to ameliorate a condition via anti-inflammatory, antioxidant, autophagy, and/or anti-aging effects. In these or other embodiments, the treatment method may be used to ameliorate a condition affecting a subject's blood pressure, heart health, kidney health, immune system, circulation, liver health, endurance, skin health, eye health, cognition, elevated cholesterol, hormone balance, reproductive health, and/or digestive health.

The subject is not limited. Typically, however, the subject is an animal, such as a mammal (i.e., vertebrates of the class Mammalia, such as dogs, cats, goats, sheep, pigs, cattle, horses, donkeys, camels, and the like). Additional mammals that are specifically contemplated herein include semi-domesticated mammals and mammals that are routinely bred in captivity. Of course, the term mammal also encompasses humans (which may be referred to as "people" and/or "person(s)" herein). When describing a human, the term "adult" is typically used herein to refer to a human that has reached sexual maturity. By contrast, the terms "child" and "juvenile" are used herein to refer to a human that has not yet reached sexual maturity. Typically, the term "child" means a human subject between the stage of birth and the age of about 10 (i.e., childhood), and the term "juvenile" means a human subject that is greater than the age of about 10 and who has not completed the stage of puberty. Of course, the terms child, juvenile, adult, and infant are all encompassed by the term "human", which is itself a subcategory of mammal, which is a subcategory of animal as defined herein.

The protein hydrolysate composition may be administered to the subject in any form. Typically, the protein hydrolysate composition is administered orally and/or topically (e.g. as the consumable and/or topical formulations described above). However, other routes of administration may also be utilized.

When formulated for oral administration, the protein hydrolysate composition may be presented in discrete units (e.g. capsules, cachets, lozenges, tablets, etc.), each containing a predetermined amount of the protein hydrolysate composition (e.g. a recommended dose). For example, such unit doses may be utilized when the protein hydrolysate composition is formulated as the food additive and/or nutritional supplement. However, the protein hydrolysate composition may compose any form, such as a dry powder, a solution, a suspension, an emulsion, or the like, which may be presented in bulk form. For example, in certain embodiments, the protein hydrolysate composition formulated as the dry powder. In such embodiments, the treatment method may comprise measuring a dose of the protein hydrolysate composition to be administered, mixing the dose with foodstuff to form the food or beverage comprising the protein hydrolysate composition, and orally administering the food or beverage to the subject. In certain embodiments, as described above, the protein hydrolysate composition is adapted to be consumed as a liquid. In such embodiments, the treatment method may include combining a dose of the dry powder with a consumable liquid (e.g. water, juice, etc.) to form a consumable liquid (e.g. solution, suspension, emulsion, etc.) comprising the protein hydrolysate composition, orally administering the consumable liquid to the subject. In these or other embodiments, the dose of the protein hydrolysate composition to be administered may be pre-mixed with the foodstuff to form a food or beverage product comprising the protein hydrolysate composition, which may be subsequently consumed by the subject (e.g. via assisted, supervised, or self-administration).

When formulated for topical oral administration (i.e., as the topical composition), the protein hydrolysate composition may be presented in discrete units (e.g. pouches, packets, pods, etc.), each containing a predetermined amount of the protein hydrolysate composition (e.g. a recommended dose). For example, such unit doses may be utilized when the topical composition is formulated as the ointment, paste, cream, lotion, or gel, described above. Additionally, such unit doses may presented as a patch, i.e., with a unit dose of the topical composition in one of the forms above disposed on a backing member, which is adapted to support and secure the protein hydrolysate composition to a surface of the subject. The topical composition may also be presented in bulk form, such that the treatment method may comprise measuring a dose of the topical composition to be administered before administration. Examples of bulk forms include multi-dose amounts of the topical composition combined in a single container (e.g. a tub, jar, tube, can, etc.). Such containers may comprise a dispenser, such as in the case of a pump jar, lotion dispenser, pump spray jar, etc., such that measuring the dose of the topical composition is made convenient to the subject or a person administering the topical composition thereto.

The protein hydrolysate composition, in any form, may be administered as needed, daily, several times per day or in any suitable regimen such that a desired outcome is achieved. In the treatment method, the frequency of administration can depend on several factors, including the desired level of prevention or amelioration. Generally, a regimen includes administration of the protein hydrolysate composition to the subject once or twice daily, e.g. includes an administration in the morning and/or an administration in the evening. The amount of protein hydrolysate administered to the subject during each administration (i.e., the dose) may depend on several factors, such as the level of results desired, and the specific composition being utilized, the number of doses being administered, etc. In general, the protein hydrolysate composition is administered in a therapeutically or physiologically effective amount. As used herein, the term "therapeutically effective amount" relates to an amount (i.e., a quantity) of a composition (e.g. the protein hydrolysate composition of the present embodiments) required to achieve a particular therapeutic and/or prophylactic effect, such as in treating a subject (e.g. by ameliorating a condition thereof). Likewise, as used herein, the term "physiologically effective amount" relates to an amount of a composition (e.g. the protein hydrolysate composition of the present embodiments) required to achieve a desired physiological effect. Such effective amounts are typically measured and/or expressed in terms of the amount of the protein hydrolysate composition over time (e.g. g/day, mg/day, etc.), but may also incorporate the body weight of the subject (e.g. in kg), as expressed by the unit g/kg/day. Typically, the protein hydrolysate composition is administered in an amount effective to provide the isolated peptides of the protein hydrolysate to the subject. In certain embodiments, the protein hydrolysate composition is administered in an amount effective to ameliorate a condition of the subject. In these or other embodiments, the phytofunctional composition is administered in an amount effective to ameliorate at least two conditions of the subject.

As described above, the treatment method may be used to ameliorate a condition of the subject, such as one or more of those described above. For example, in specific embodiments, the treatment method is used to ameliorate a condition including high blood pressure, inflammation, kidney disease, oxidative stress, reduced immunity, or combinations thereof. In such embodiments, the treatment method may be further defined as a method of reducing blood pressure in the subject, reducing inflammation in the subject, enhancing immune activity in the subject, decreasing reactive oxidants in the subject, inducing vasodilation in the subject, improving or enhancing a quality of life of the subject, or combinations thereof. However, it is to be appreciated that the effect(s) of the protein hydrolysate composition may also be used preventatively, as described above, and the treatment method may thus be further defined as a method of maintaining blood pressure in the subject, preventing inflammation in the subject, maintaining immune activity in the subject, preventing oxidative stress in the subject, preventing vasoconstriction in the subject, or combinations thereof.

As will be understood in view of the Examples and description here, the treatment method may be used to ameliorate such a condition by reducing inflammation (e.g. via inhibiting proinflammatory enzymes such as lipoxygenase (LPO) and cyclo-oxygenases (COX-1, COX-2)), reducing oxidant concentration, reducing blood pressure, increasing vasodilation, enhancing immune activity, controlling blood glucose and/or lipid levels, inhibiting a stage of a cancer process (e.g. by increasing apoptosis and/or decreasing metastasis, signal transduction, transcription factor activity, cell adhesion, etc.), improving visual function, and the like, or combinations thereof. For example, in particular embodiments, the method is be used to ameliorate a condition by inhibiting or reducing the activity of angiotensin converting enzyme (ACE) in the subject, activating NAD(P)H:quinone reductase (QR) in the subject, reducing expression of messenger ribonucleic acid (mRNA) for renin in the subject, inducing a drug-metabolizing enzyme in the subject, activating nuclear factor erythroid 2 (NFE2)-related factor 2 (NRF2) in the subject, or combinations thereof. It is to be appreciated that administration of the protein hydrolysate composition may be used to supplement in vivo mediation of such enzymes as well.

The following examples are intended to illustrate the invention and are not to be viewed in any way as limiting to the scope of the invention.

EXAMPLE 1

Preparation of Protein Hydrolysate Composition Comprising Isolated Peptides

Hydrolysis of Sunflower Seed Protein

Protein material (sunflower protein isolate, 55% protein content) is dispersed in distilled water in a 1000 mL reactor fitted with temperature and pH control devices to obtain a 10% (w/v) slurry in the reactor. The slurry is heated to 50° C. and pH was adjusted to 6.8. A protease (Flavourzyme) is then added at a ratio of 4% (on the basis of protein weight, w/w) to give a reaction mixture. The temperature of the reaction mixture is maintained at constant value for 4 h, during which time the pH of the reaction mixture is maintained at 6.8 by addition of liquid sodium hydroxide (NaOH) as necessary. The hydrolysis reaction is stopped by heating to and holding at 95° C. for 15 min to give a whole hydrolysis reaction product, which is freeze dried until further used. The whole hydrolysis reaction product is centrifuged (10,000×g, 20 min) to give a soluble supernatant fraction and a residual fraction, and the soluble supernatant fraction collected to give a crude hydrolysate, which is freeze dried until further used.

Characterization of the Crude Hydrolysate

The crude hydrolysate is analyzed via size exclusion chromatography to determine the average molecular weight distribution of the peptides therein. The results of the molecular mass distribution analysis is set forth in Table 1 below.

TABLE 1

Average Molecular Weight Distribution of Hydrolysis Reaction Products

| MW (kD) | Crude Hydrolysate % | Whole Hydrolysis Reaction Product % | Residual Fraction % |
|---|---|---|---|
| <1 | 57.2 | 72 | 82.9 |
| 1-3 | 7.1 | 8.5 | 7.4 |
| 3-5 | 3.2 | 2.6 | 1.7 |
| 5-10 | 10.8 | 5.4 | 3 |
| 10-20 | 14.7 | 8.8 | 4.6 |
| >20 | 7 | 2.9 | 0.2 |
| Average MW (Daltons): | 235 | 224 | 194 |

Purification of the Crude Reaction Product

Figure 2:
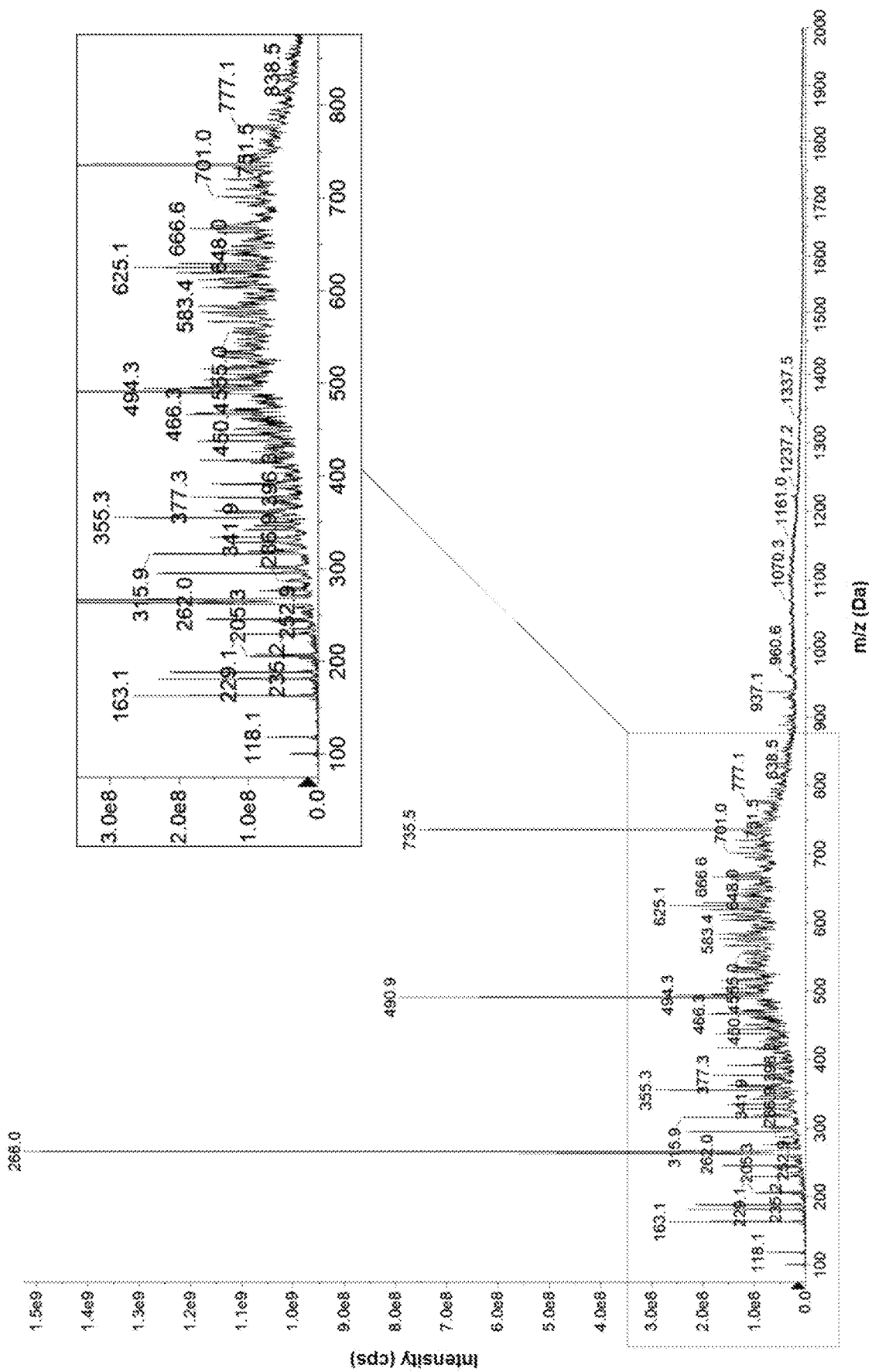
FIG. 2 provides a mass spectrometer analysis of a protein hydrolysate composition.
Figures 6A, 6B, 6C, 6D:
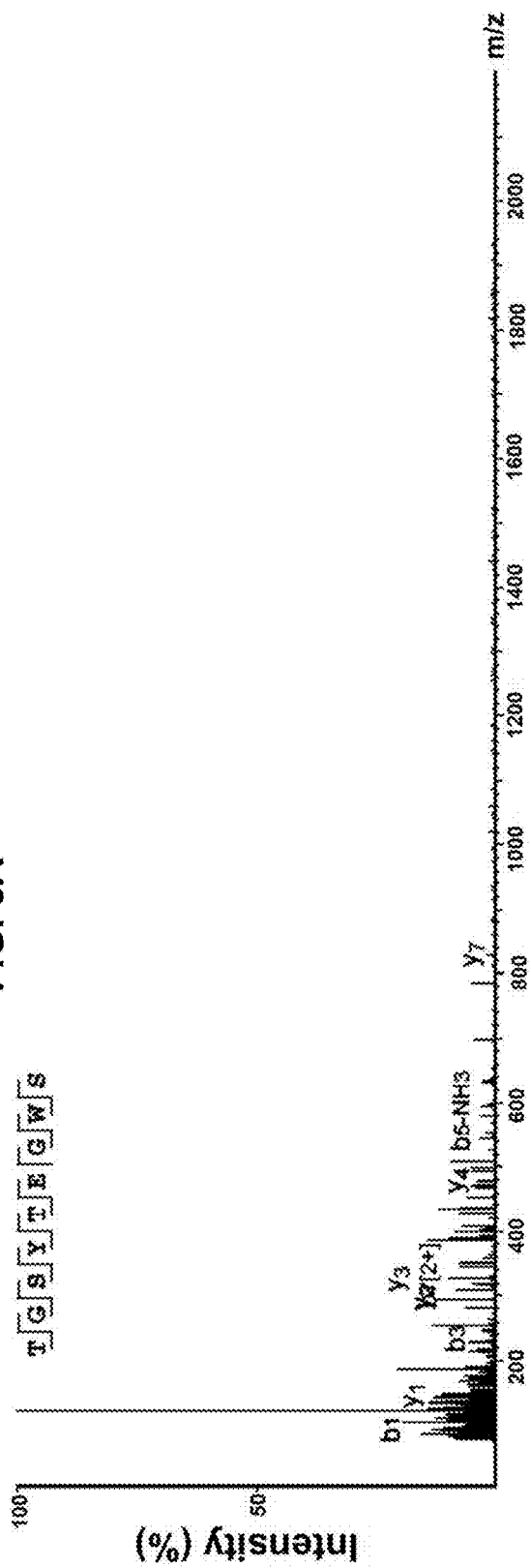
FIGS. 6A-6D provide amino acid sequence data for an isolated peptide "TGSYTEGWS" as SEQ ID NO: 4, with a mass spectrum of a fraction of the protein hydrolysate composition shown in FIG. 6A as well as a corresponding ion table shown in FIG. 6B, fragment map shown in FIG. 6C, and mass error mapping shown in FIG. 6D.

The crude reaction product is fractionated by preparative reverse-phase HPLC using a linear gradient elution from solvent A (0.1% trifluoroacetic acid (TFA) in water) to solvent B (0.1% TFA in acetonitrile) over 60 min at an optimized flow rate of at least 5 mL/min. Fractions with absorbance detected at 214 nm are pooled, stripped of solvent (rotary evaporator), and freeze-dried, to give 9 pooled fractions comprising isolated peptides. The HPLC absorbance spectrograph is set forth in FIG. 1. Fraction 7 is collected to give a protein hydrolysate composition, which is then analyzed via mass spectrometry (MS). The results of the MS analysis of the protein hydrolysate composition are set forth in FIG. 2.

Characterization of the Isolated Peptides in the Protein Hydrolysate Composition The protein hydrolysate composition is dissolved (0.1% formic acid in water), and the resulting solution purified via Ultra Performance Liquid Chromatography (UPLC) using an ACQUITY UPLC system (Waters, Milford, Mass.) equipped with Eclipse Plus C18 RRHD columns (2.1×100 mm, 1.8 μm, ZORBAX, U.S.) and operated at a linear gradient of 30% acetonitrile to give isolated peptides 1-4. Each of the isolated peptides is sequence analyzed via ESI-MS (quadrupole mass spectrometer coupled with electrospray ionization, Micromass, Waters, U.S.). The results of the sequence analyses are set forth in FIGS. 3A-D, 4A-D, 5A-D, and 6A-D. Each of the peptide sequences is then synthesized by a commercial supplier (Genscript USA Inc., Piscataway, United States) to give additional samples (>95% purity).

EXAMPLES 2 & 3 AND COMPARATIVE EXAMPLE 1

NFκB-luciferase Reporter Gene Assay

Figure 7:
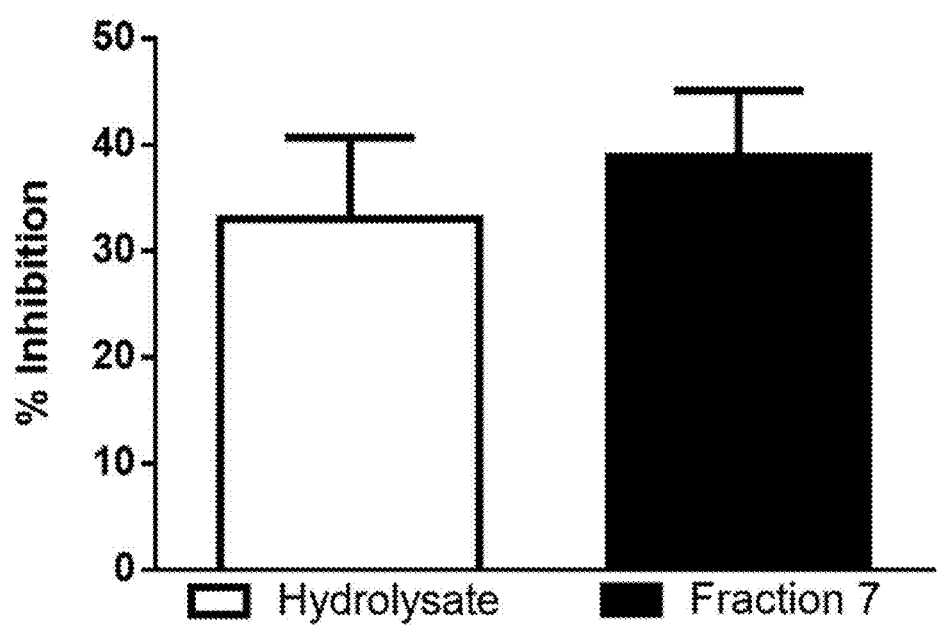
FIG. 7 provides results of a nuclear factor kappa-light-chain-enhancer of activated B cells (NF-κB) reporter gene assay performed on protein hydrolysate compositions prepared in accordance with the subject disclosure.

Human A549 cells are stably transfected with a pNFκB-Luc plasmid (Clontech, Mountain View, Calif.) using Fugene 6 transfection reagent (Promega, Madison, Wis.). To assess anti-inflammatory activity of samples, the cells are plated at 5×104/well in white, 96 well, clear bottom microtiter plates and incubated overnight in OptiPro serum-free media. The following day, the cells are exposed to samples (crude hydrolysate and the protein hydrolysate composition of Fraction 7 of Example 1, each at a concentration of 250 μg/mL) and IL-1β (100 μg/mL). Six hours after addition of IL-1β the cells are lysed, and the relative amount of luciferase is assessed using luciferin reagents from Biotium (Hayward, Calif.). The results of the assay are set forth in FIG. 7, with data expressed as percent control, in which the relative luminescence units elicited by control cells exposed only to IL-1β is set at 100%.

EXAMPLES 4-5 & COMPARATIVE EXAMPLES 2-3

Co-Stimulatory Molecule Expression (Cluster of Differentiation (CD)) Assay

Figure 8A:
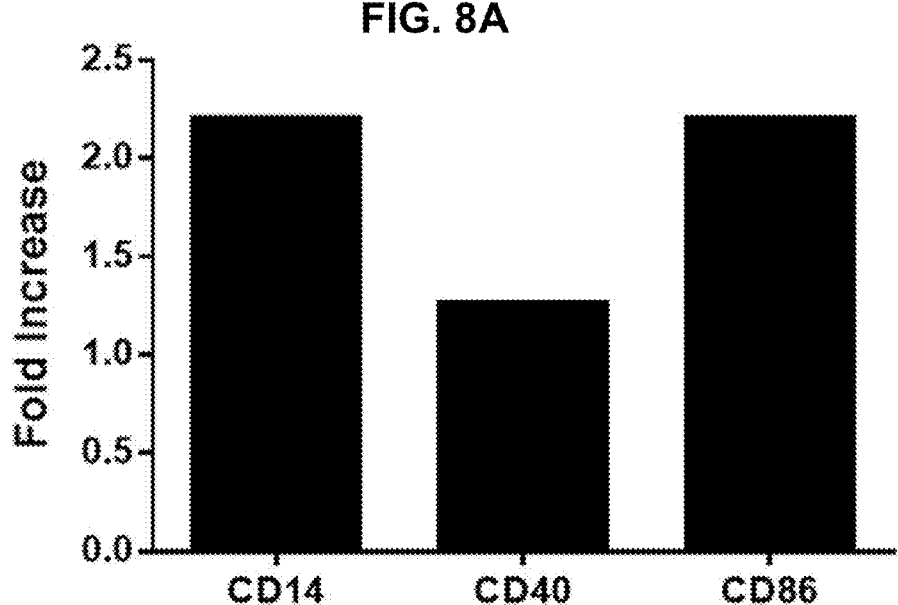
FIGS. 8A-8D provide results of a Cluster of Differentiation (CD) assay performed on protein hydrolysate compositions prepared in accordance with the subject disclosure, with FIG. 8A showing a graph of CD14, CD40, and CD86 assay results one protein hydrolysate composition, and FIGS. 8B-8D showing relative CD14, CD86, and CD40 assay results, respectively, for another protein hydrolysate composition.
Figure 8B:
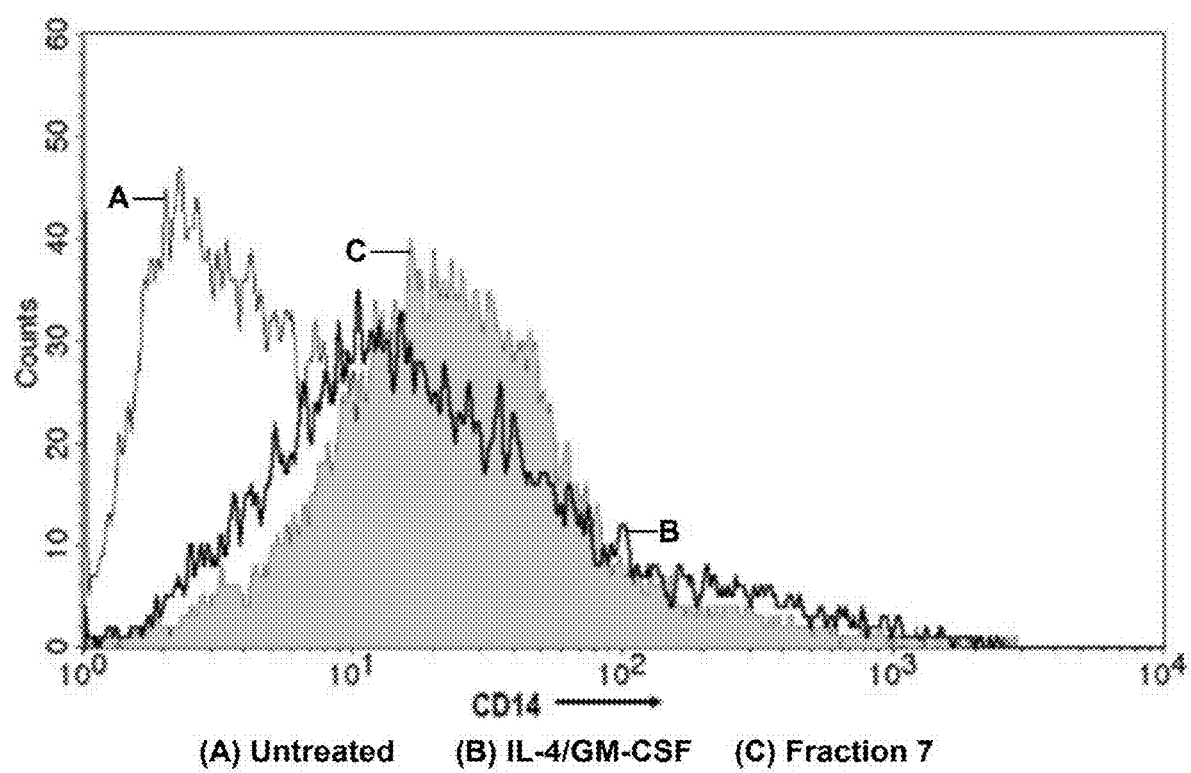
Figure 8C:
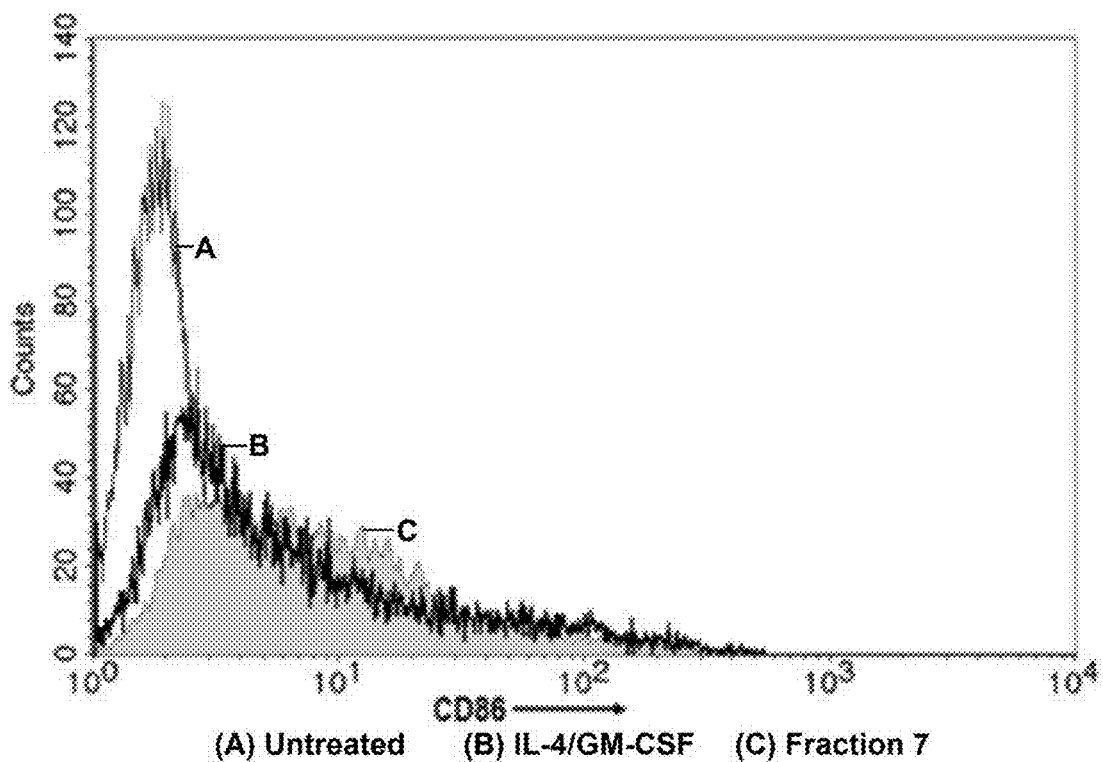
Figure 8D:
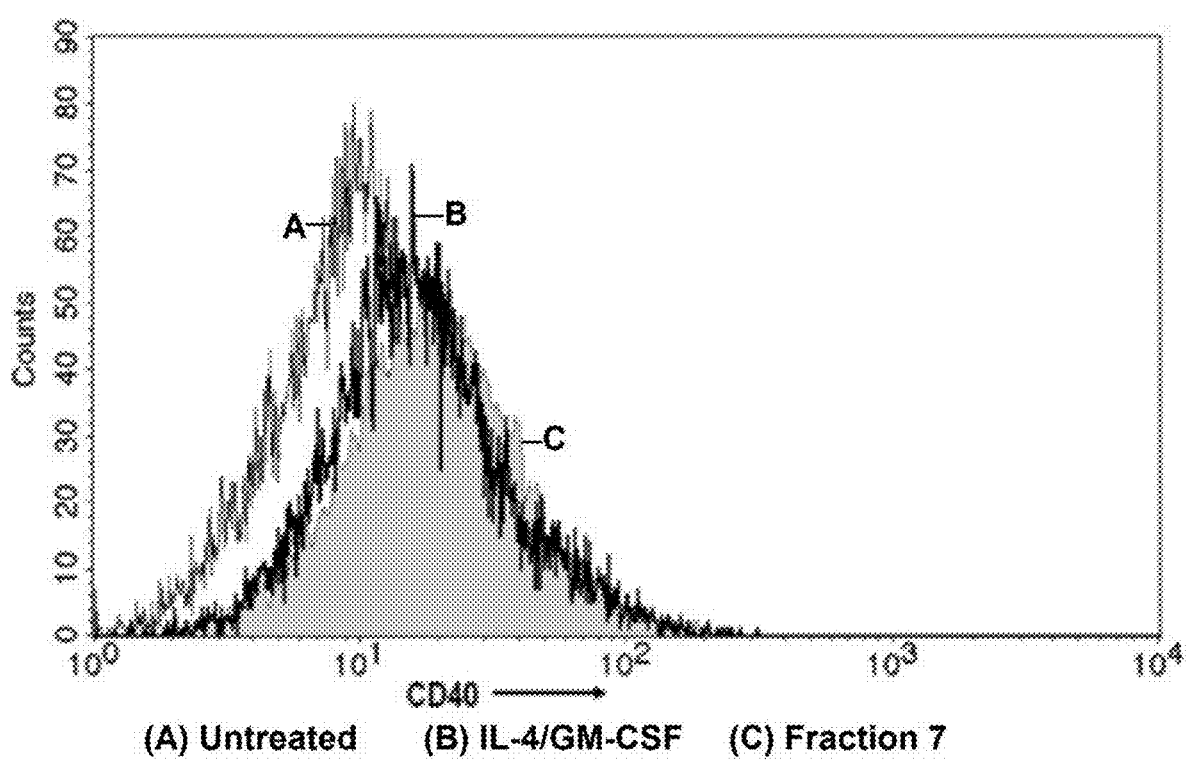

THP-1 cells are plated at 2×106/well in 6 well plates in a volume of 2 mL for 120 h. Samples (crude hydrolysate and the protein hydrolysate composition of Fraction 7 of Example 1) are added to the cells and left for 48 h, and then one half of the media is removed and replaced with an equal volume of fresh media and additional sample. A combination of interleukin-4 (IL-4) and Granulocyte-Macrophage Colony Stimulating Factor (GM-CSF) (5 ng/mL each) is used as positive control with additions at 0 and 48 h. Cells are collected using PBS-EDTA (2 mM) with gentle repeated pipetting to dislodge the cells from the culture well surface. The cells are stained for 1 h at 4° C. with anti-human-CD14-PE, -CD40-Alexa Fluor® 488, or -CD80-PerCP/Cy5.5 Alexa Fluor® 488 antibody according to the manufacturer's specifications, and then washed three times with cold PBS. Fluorescence is assessed by flow cytometry on a Becton Dickinson FACSCaliber. The results of the assay are set forth in FIG. 8A-D, where FIG. 8A represents the results using the crude hydrolysate (100 μg/mL), and FIGS. 8B-D represent the results of using the protein hydrolysate composition of Fraction 7 (100 μg/mL).

EXAMPLES 6 & 7

Nuclear Factor (Erythroid-Derived 2)-like 2 (NRF-2) Assay

Figure 9:
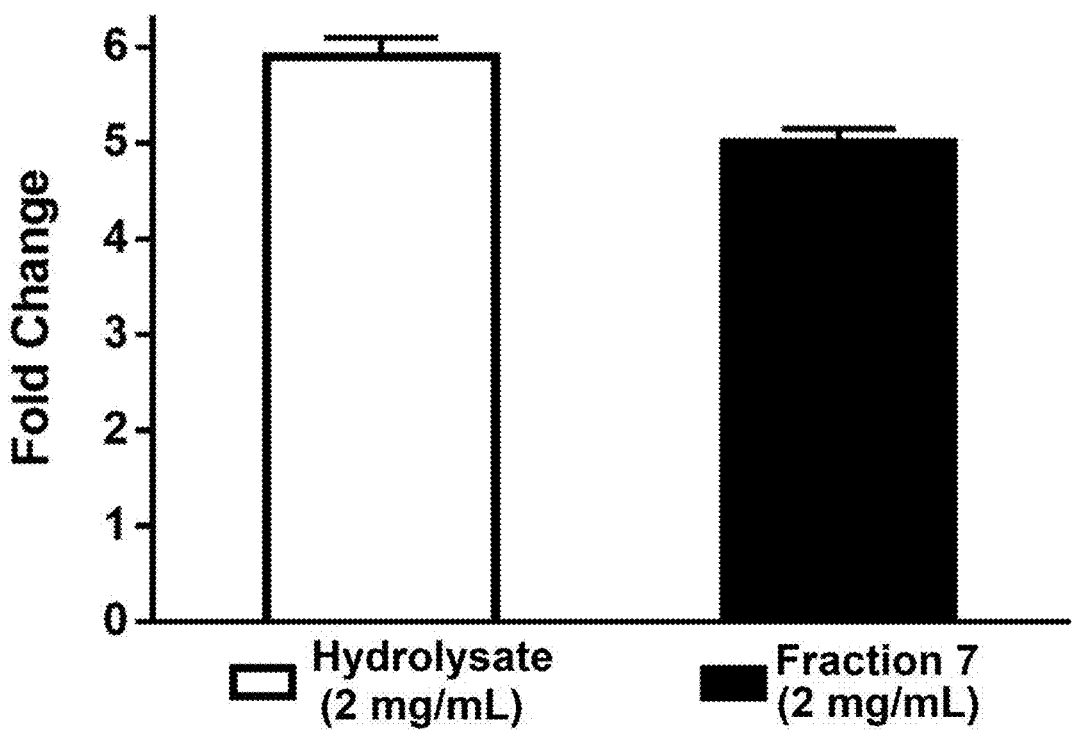
FIG. 9 provides results of a Nuclear Factor Erythroid 2-Related Factor 2 (NRF-2) activation assay performed on protein hydrolysate compositions prepared in accordance with the subject disclosure.

Four repeats of the Antioxidant Response Element (5'-GTGACTCAGCA-3' (SEQ ID NO: 5)) oligonucleotide and its complementary sequence are hybridized and ligated in to the SacI/BglII sites of the pGL4.27[luc2P/minP/Hygro] vector (Promega, Madison, Wis.). The resulting plasmid is transfected in to HepG2 cells using FuGENE 6 (Promega) to generate stable cell lines. Samples (crude hydrolysate and the protein hydrolysate composition of Fraction 7 of Example 1) are added to the cells incubated for 48 h. After treatment, luciferase activity is quantified using a luciferase assay kit (Biotium, Fremont, Calif.). Briefly, cells are rinsed with 50 μL of DPBS, and then lysed with 20 μL lysis buffer for 20 m at room temperature. D-luciferin is added, and light emission is read immediately on a SpectraMax M5 spectrophotometer plate reader. The results of the assay are set forth in FIG. 9.

EXAMPLES 8 & 9

Quinone Reductase (QR) Assay

Figure 10:
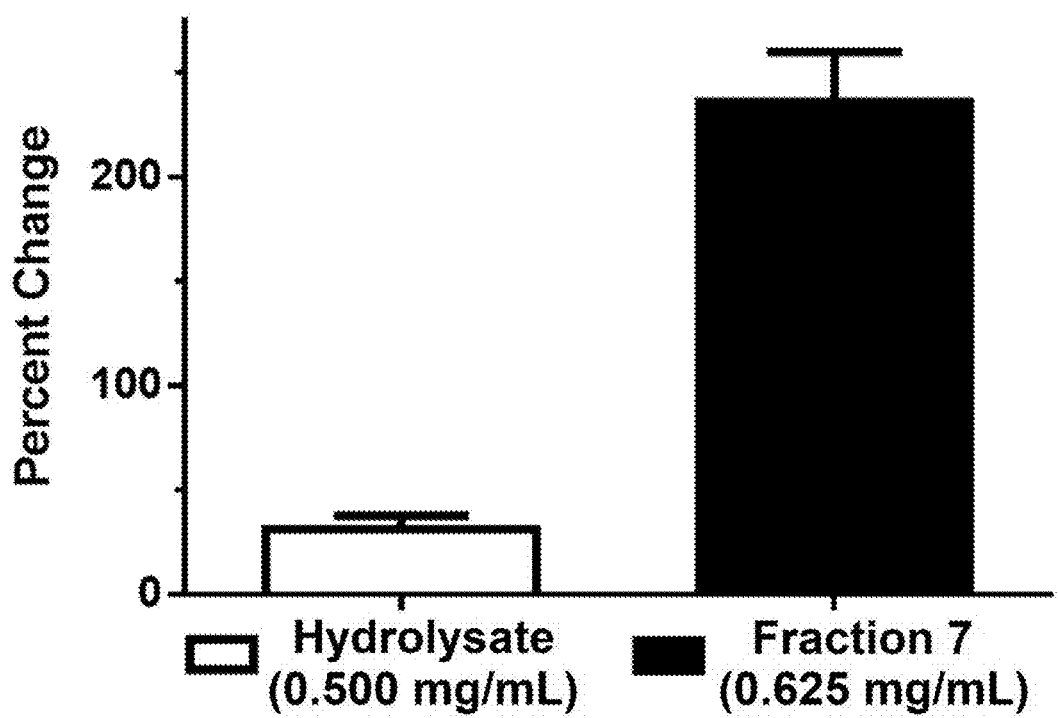
FIG. 10 provides results of a Quinone Reductase (QR) activation assay performed on protein hydrolysate compositions prepared in accordance with the subject disclosure.

Hepa1c1c7 cells are plated in 96-well plates and incubated overnight. The cells are then treated for 24 h with samples (crude hydrolysate and the protein hydrolysate composition of Fraction 7 of Example 1). Following treatment, the cells are washed with room temperature PBS, lysed with 0.8% digitonin (50 μL) for 10 min at 37° C., and then shaken for 10 min at room temperature. Quinone reductase activity is assayed by adding reaction buffer (200 μL) to the lysate, incubating at room temperature for approximately 4 min, terminating the reaction with stop solution, and reading absorbance at 610 nm on a SpectraMax M5 spectrophotometer. The results of the assay are set forth in FIG. 10.

EXAMPLES 10 & 11

2,2-Diphenyl-1-picryl-hydrazyl-hydrate (DPPH) Assay

The scavenging activity of crude hydrolysate and the protein hydrolysate composition of Fraction 7 against DPPH is determined by first dissolving samples (crude hydrolysate and the protein hydrolysate composition of Fraction 7 of Example 1) in 0.1 M sodium phosphate buffer, pH 7.0 containing 1% (w/v) Triton X-100. DPPH is dissolved in methanol to a final concentration of 100 µM, and mixed with the samples in the 96-well plate to a final assay concentration of 1 mg/mL. The samples are then incubated at room temperature in the dark for 30 min, and the absorbance read at 517 nm. The results of the assay are set forth in Table 2 below.

EXAMPLES 12 & 13

Hydroxyl Radical Scavenging Activity (HRSA) Assay

The hydroxyl radical scavenging activity of crude hydrolysate and the protein hydrolysate composition of Fraction 7 is determined by dissolving samples (crude hydrolysate and the protein hydrolysate composition of Fraction 7 of Example 1) and 1,10-phenanthroline in 0.1 M sodium phosphate buffer (pH 7.4). FeSO4 (3 mM) and 0.01% hydrogen peroxide are separately dissolved in distilled water. An aliquot (50 µL) of samples (final assay concentration of 0.5 mg/mL) or buffer (control) is first added to a clear, flat bottom 96-well plate followed by additions of 50 µL of 1,10-phenanthroline and 50 µL of FeSO4. To initiate reaction in the wells, 50 µL of hydrogen peroxide (H2O2) solution is added to the mixture, which is then covered and incubated at 37° C. for 1 h with shaking. Absorbance is measured at 536 nm every 10 min for a period of 1 h. The results of the assay are set forth in Table 2 below.

TABLE 2

| DPPH Radical Scavenging and Hydrogen Radical Scavenging Activity (HRSA) | | |
|---|---|---|
| | DPPH (% ± SD) | HRSA (% ± SD) |
| Crude Hydrolysate | 39.05 ± 1.05 | 134.29 ± 9.91 |
| Fraction 7 | 51.07 ± 1.11 | 0.91 ± 0.37 |

EXAMPLES 14 & 15

Nitric Oxide (NO) Production Assay

Figure 11:
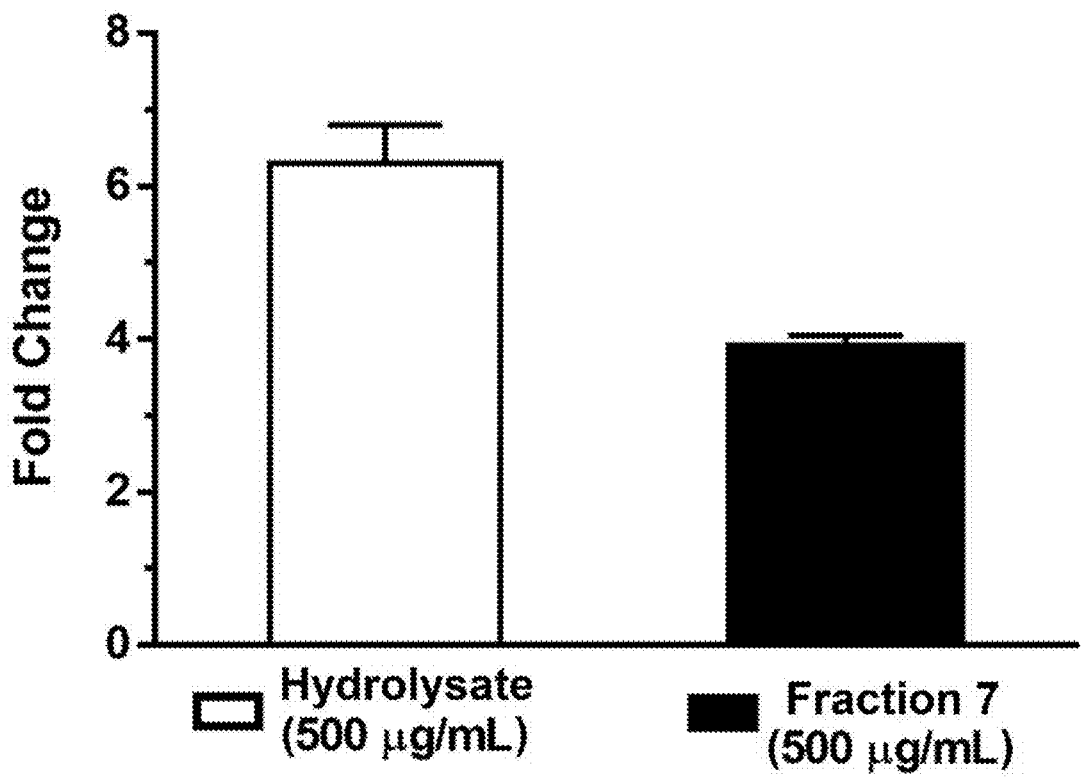
FIG. 11 provides results of a Nitric Oxide (NO) Production assay performed on protein hydrolysate compositions prepared in accordance with the subject disclosure.

NO production is measured in HUVAC by fluorescence using Daf-FM Diacetate and Fluorobrite. Cells are plated in 96-well collagen coated plates and incubated for 48 h. Daf-FM is dissolved in Fluorobrite (10 µM) and then added to each well and incubated for 30 min at 37° C., followed by sample treatment (crude hydrolysate and the protein hydrolysate composition of Fraction 7 of Example 1) for 24 h. Fluorescence (excitation 485 nM, emission 515 nM) is measured on a SpectraMax M5 spectrophotometer. The results of the assay are set forth in FIG. 11.

EXAMPLES 16 & 17

ACE Inhibition Assay

The ability of sample to inhibit in vitro activity of ACE is determined by mixing 1 mL of FAPGG (0.5 mM, dissolved in buffer [50 mM Tris-HCl buffer containing 0.3 M NaCl, pH 7.5]) with 20 µL ACE (1 U/mL, final activity of 20 mU) and 200 µL sample (crude hydrolysate and the protein hydrolysate composition of Fraction 7 of Example 1, each dissolved in buffer to 1 mg/mL). The rate of decrease in absorbance at 345 nm is recorded for 2 min at room temperature. The results of the assay are set forth in Table 3 below, expressed as percent inhibition.

EXAMPLES 18 & 19

Renin Inhibition Assay

In vitro inhibitory activity of human recombinant renin is conducted using a Renin Inhibitor Screening Assay Kit. Samples (crude hydrolysate and the protein hydrolysate composition of Fraction 7 of Example 1) are diluted in Tris-HCl buffer (50 mM, pH 8.0, containing 100 mM NaCl) to a final concentration 0.5 mg/mL, and pre-warmed to 37° C. The reaction is initiated by adding renin (10 µL), shaking for 10 s to mix, and incubating at 37° C. for 15 min. Fluorescence intensity (FI) is then recorded at an excitation wavelength of 340 nm and an emission wavelength of 490 nm using a fluorometric microplate reader. The results of the assay are set forth in Table 3 below, expressed as percent inhibition.

TABLE 3

| Percent Inhibition of ACE and Renin Activity | | |
|---|---|---|
| | ACE (% ± SD) (0.5 mg/mL) | Renin (% ± SD) (1 mg/mL) |
| Crude Hydrolysate | 54.91 ± 1.07 | 47.61 ± 1.46 |
| Fraction 7 | 72.01 ± 1.26 | 38.58 ± 1.99 |

EXAMPLES 20-23

Individual Nuclear Factor (Erythroid-Derived 2)-like 2 (NRF-2) Assays

Figure 12:
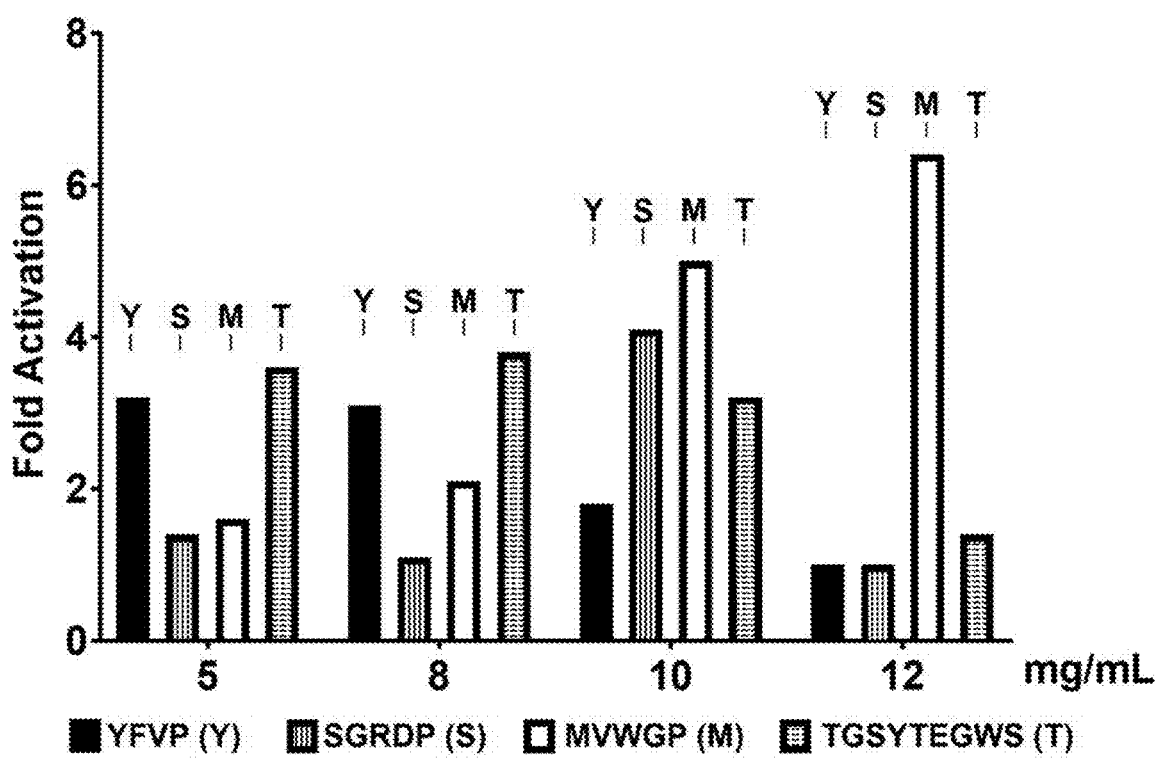
FIG. 12 provides results of a Nuclear Factor Erythroid 2-Related Factor 2 (NRF-2) activation assay performed on additional protein hydrolysate compositions prepared in accordance with the subject disclosure.
Figure 13:
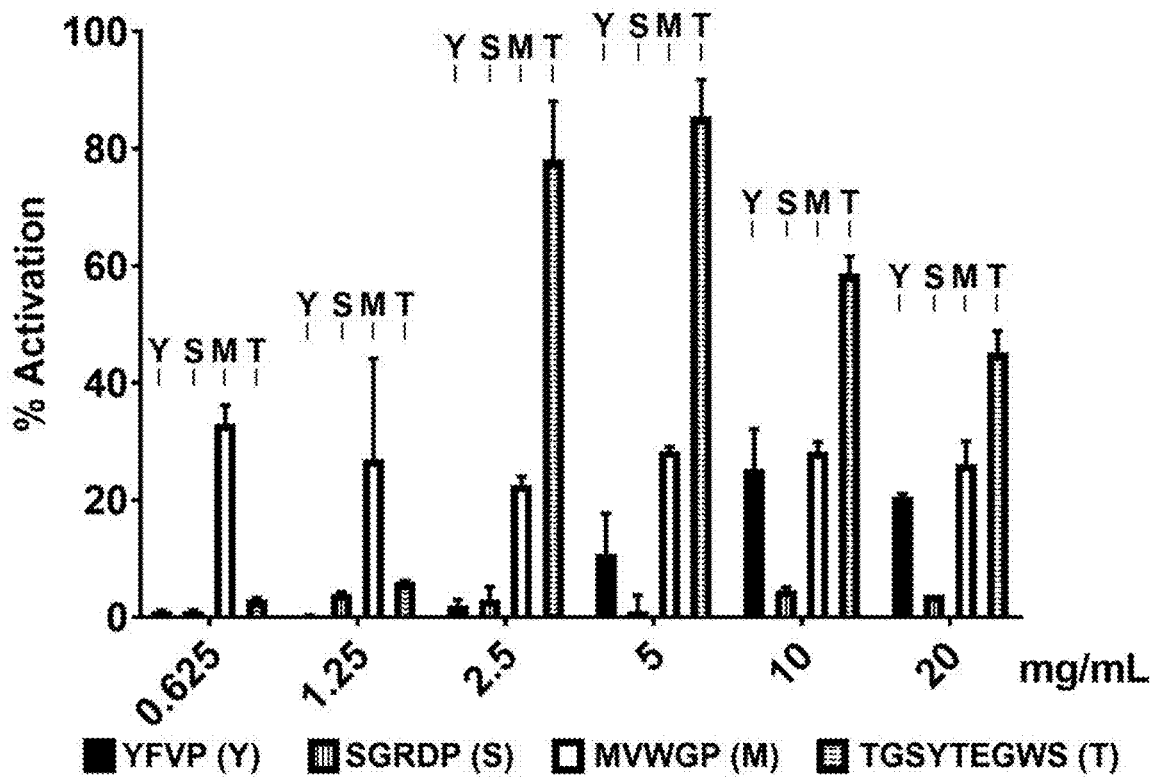
FIG. 13 provides results of a Quinone Reductase (QR) activation assay performed on additional protein hydrolysate compositions prepared in accordance with the subject disclosure.

The procedure set forth above for Examples 6 & 7 is repeated using samples containing one of the isolated peptides 1-4 of Fraction 7 of Example 1. The results of the assays are set forth in FIG. 12.

EXAMPLES 24-27

Individual Quinone Reductase (QR) Assays

The procedure set forth above for Examples 8 & 9 is repeated using samples containing one of the isolated pep-

EXAMPLES 28-31

Individual 2,2-Diphenyl-1-picryl-hydrazyl-hydrate (DPPH) Assays

The procedure set forth about for Examples 10 & 11 is repeated using samples containing one of the isolated peptides 1-4 of Fraction 7 of Example 1. The results of the assay are set forth in Table 4 below.

TABLE 4

Individual DPPH Radical Scavenging Activities

| Peptide # | Sequence | SEQ ID NO: | $IC_{50}$ (mg/mL ± SD) |
|---|---|---|---|
| 1 | YFVP | 1 | 3.85 ± 0.13 |
| 2 | SGRDP | 2 | 28.340 ± 0.38 |
| 3 | MVWGP | 3 | 4.69 ± 0.05 |
| 4 | TGSYTEGWS | 4 | 4.26 ± 0.03 |

EXAMPLES 32-35

Individual Hydroxyl Radical Scavenging Activity (HRSA) Assays

The procedure set forth above for Examples 12 & 13 is repeated using samples containing one of the isolated peptides 1-4 of Fraction 7 of Example 1. The results of the assay are set forth in Table 5 below.

TABLE 5

Individual Hydrogen Radical Scavenging Activities

| Peptide # | Sequence | SEQ ID NO: | $IC_{50}$ (mg/mL ± SD) |
|---|---|---|---|
| 1 | YFVP | 1 | 1.93 ± 0.02 |
| 2 | SGRDP | 2 | 1.90 ± 0.08 |
| 3 | MVWGP | 3 | 2.50 ± 0.03 |
| 4 | TGSYTEGWS | 4 | 1.84 ± 0.01 |

EXAMPLES 36-39

Individual Nitric Oxide (NO) Production Assays

Figure 14:
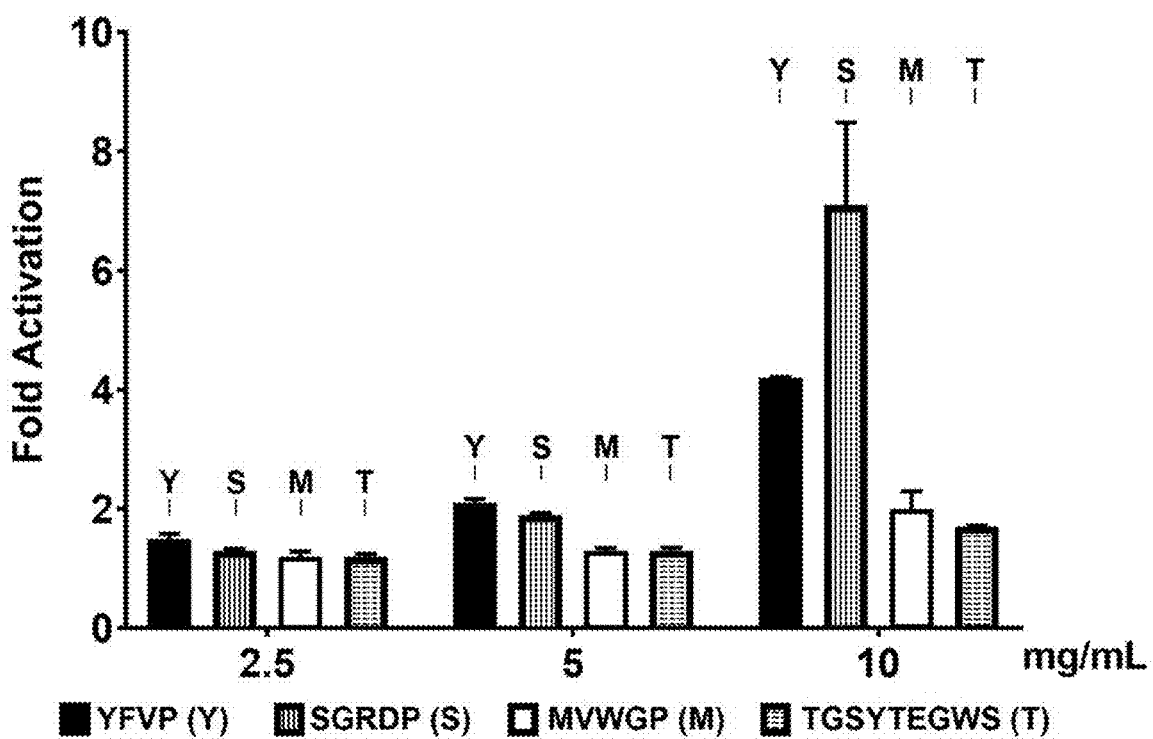
FIG. 14 provides results of a Nitric Oxide (NO) Production assay performed on additional protein hydrolysate compositions prepared in accordance with the subject disclosure.

The procedure set forth above for Examples 14 & 15 is repeated using samples containing one of the isolated peptides 1-4 of Fraction 7 of Example 1. The results of the assays are set forth in FIG. 14.

EXAMPLES 40-43

Individual ACE Inhibition Assays

The procedure set forth above for Examples 16 & 17 is repeated using samples containing one of the isolated peptides 1-4 of Fraction 7 of Example 1. The results of the assay are set forth in Table 6 below.

TABLE 6

Percent Inhibition of ACE Activity

| Peptide # | Sequence | SEQ ID NO: | $IC_{50}$ (mg/mL ± SD) |
|---|---|---|---|
| 1 | YFVP | 1 | 0.25 ± 0.05 |
| 2 | SGRDP | 2 | 0.51 ± 0.001 |
| 3 | MVWGP | 3 | 0.021 ± 0.00 |
| 4 | TGSYTEGWS | 4 | 0.55 ± 0.01 |

EXAMPLES 44-47

Individual Renin Inhibition Assays

The procedure set forth above for Examples 18 & 19 is repeated at 1 mg/mL concentrations using samples containing one of the isolated peptides 1-4 of Fraction 7 of Example 1. The results of the assay are set forth in Table 7 below.

TABLE 7

Percent Inhibition of Renin Activity

| Peptide # | Sequence | SEQ ID NO: | % Inhibition ± SD) |
|---|---|---|---|
| 1 | YFVP | 1 | -40.55 ± 6.23 |
| 2 | SGRDP | 2 | -54.50 ± 1.48 |
| 3 | MVWGP | 3 | -46.37 ± 1.56 |
| 4 | TGSYTEGWS | 4 | 106.7 ± 17.65 |

EXAMPLES 48-49 & COMPARATIVE EXAMPLE 4

NFκB-luciferase Reporter Gene Assays

Figure 15A:
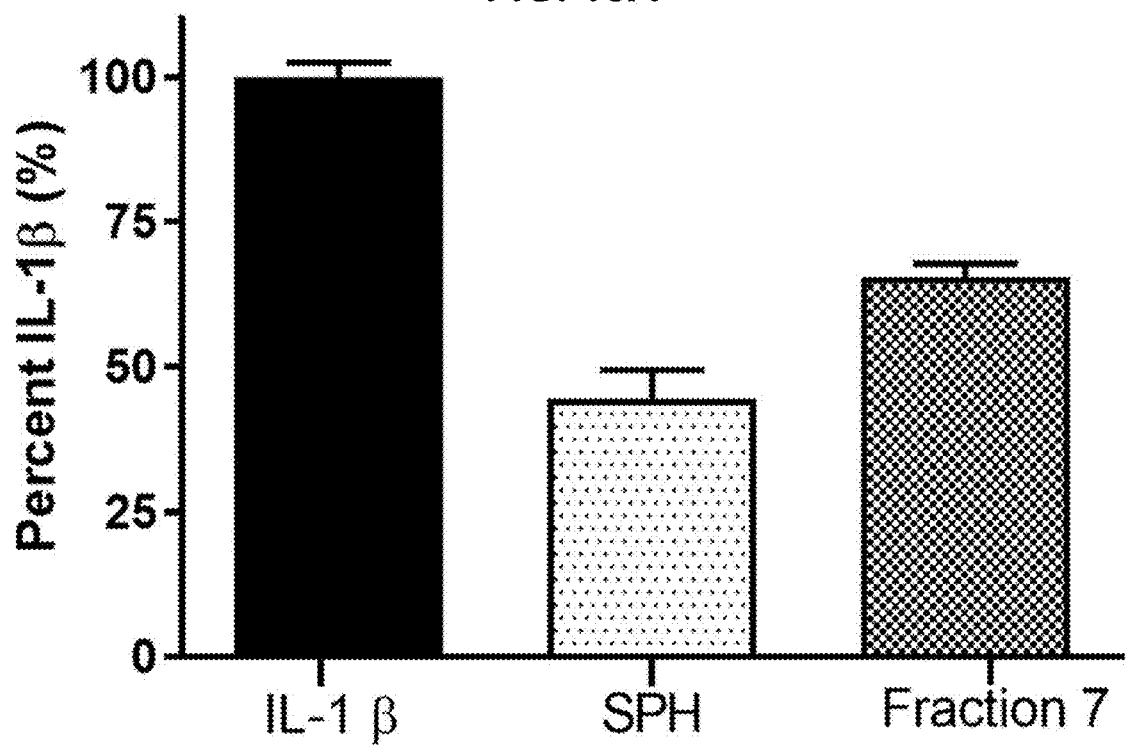
FIGS. 15A and 15B provide results of a nuclear factor kappa-light-chain-enhancer of activated B cells (NF-κB) reporter gene assay performed on additional protein hydrolysate compositions prepared in accordance with the subject disclosure, with FIG. 15A showing relative inhibition of IL-1β activated NFκB promoter activity of two protein hydrolysate compositions, and FIG. 15B showing relative inhibition of IL-1β activated NFκB promoter activity of isolated peptides of SEQ ID NOS 1-4, respectively, in order of appearance from left to right.

The procedure set forth above for Examples 2-3 is repeated with additional samples (crude hydrolysate and the protein hydrolysate composition of Fraction 7 of Example 1, each at a concentration of 250 µg/mL) and IL-1β (100 µg/mL). The results of the assay showing inhibition of IL-1β activated NFκB promoter activity are set forth in FIG. 15A, where the crude hydrolysate is labeled as "SPH", and data are expressed as a percent of IL-1β treatment activity, which is set at 100%.

EXAMPLES 50-53 & COMPARATIVE EXAMPLE 5

Individual NFκB-luciferase Reporter Gene Assays

Figure 15B:
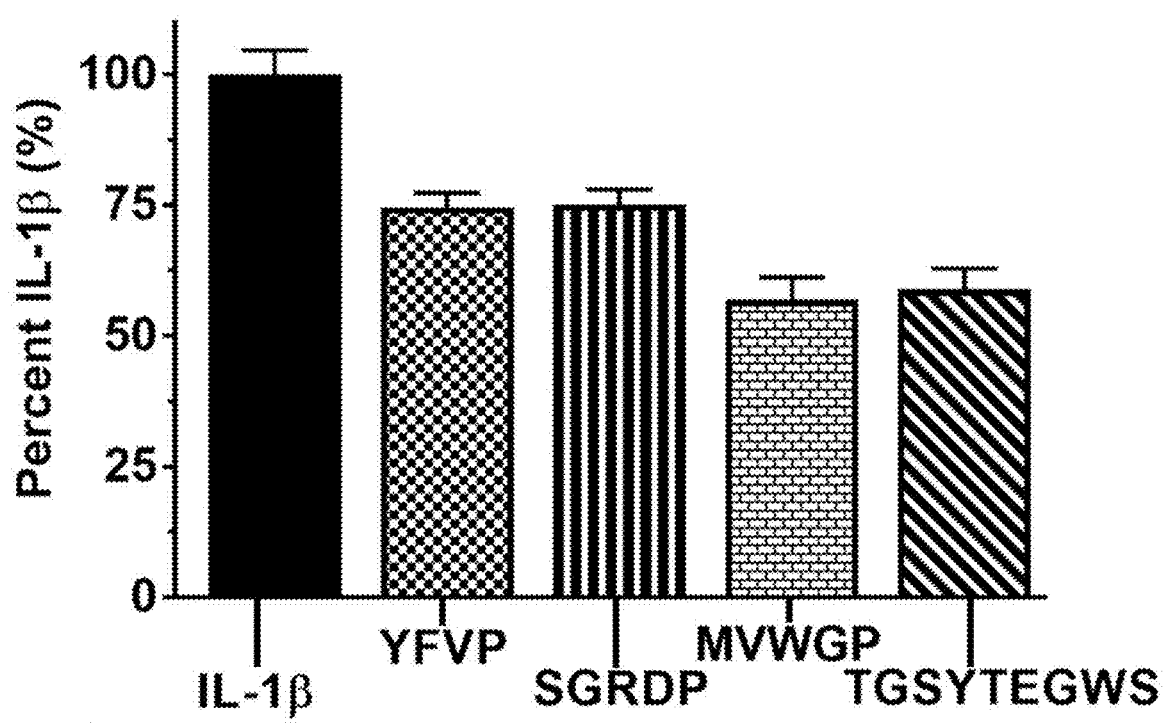

The procedure set forth above for Examples 48-49 is repeated at 250 µg/mL concentrations using samples containing one of the isolated peptides 1-4 of Fraction 7 of Example 1, and IL-1β (100 µg/mL). The results of the assay showing inhibition of IL-1β activated NFκB promoter activity are set forth in FIG. 15B, where data are expressed as a percent of IL-1β treatment activity, which is set at 100%.

EXAMPLES 54-55 & COMPARATIVE EXAMPLE 6

Co-stimulatory Molecule Expression Assays (CD14)

Figure 16A:
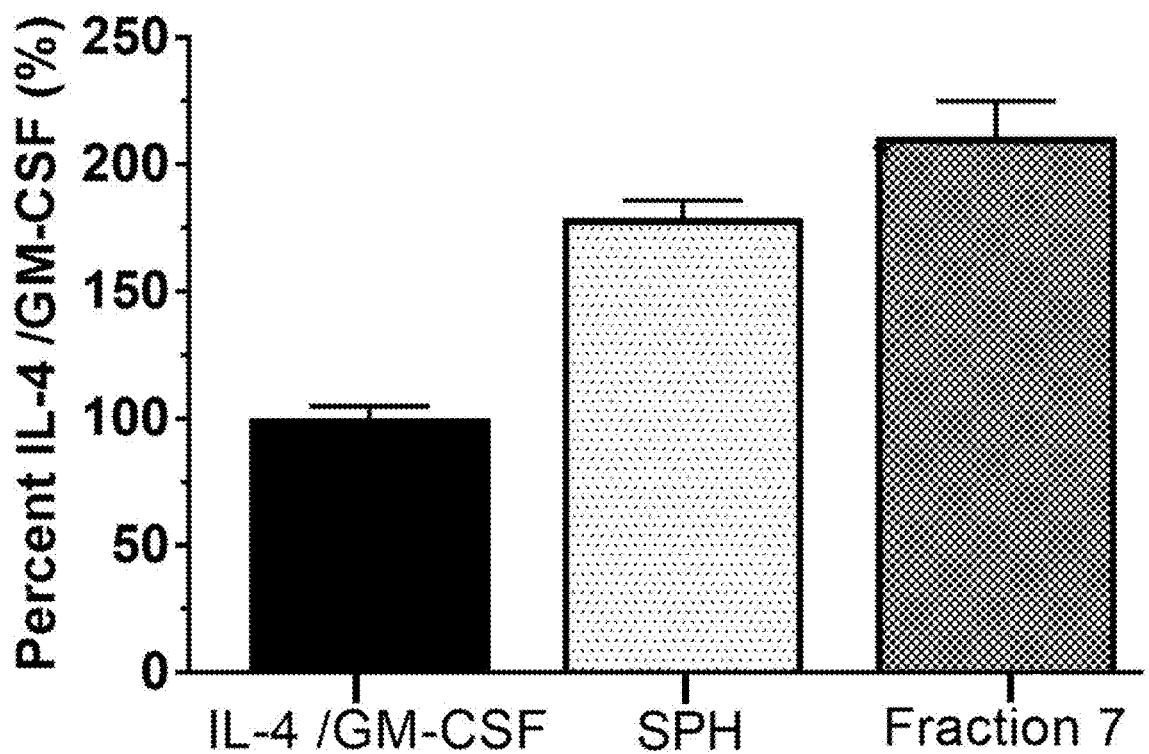
FIGS. 16A and 16B provide results of a Cluster of Differentiation 14 (CD14) assay performed on protein hydrolysate compositions prepared in accordance with the subject disclosure, with FIG. 16A showing relative CD14 assay results of two protein hydrolysate compositions, and FIG. 16B showing relative CD14 assay results of isolated peptides of SEQ ID NOS 1-4, respectively, in order of appearance from left to right.

The procedure set forth above for Examples 4-5 is repeated with additional samples (crude hydrolysate (SPH) and the protein hydrolysate composition of Fraction 7 of Example 1) at a concentration of 2 mg/mL each and IL-4 & GM-CSF at a concentration of 500 µg/mL each for 5 days, and then stained with PE anti-human CD14 antibody. The results of the CD14 assays showing the activity of the samples on IL-4/GM-CSF induced CD14 expression are set forth in FIG. 16A, where data are expressed as a percent of IL-4/GM-CSF activity, which is set at 100%.

EXAMPLES 56-59 & COMPARATIVE EXAMPLE 7

Individual Co-stimulatory Molecule Expression Assays (CD14)

Figure 16B:
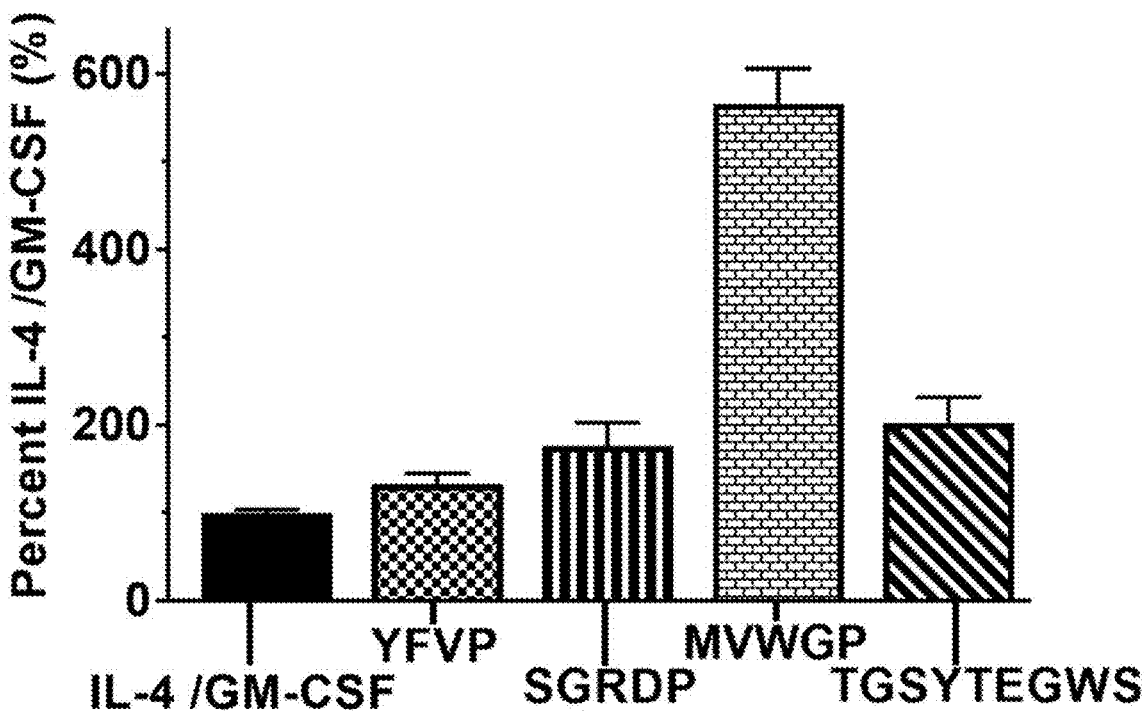

The procedure set forth above for Examples 54-55 is repeated using samples containing one of the isolated peptides 1-4 of Fraction 7 of Example 1 at concentrations of 2.5 mg/mL. The results of the CD14 assays showing the activity of the samples on IL-4/GM-CSF induced CD14 expression are set forth in FIG. 16B, where data are expressed as a percent of IL-4/GM-CSF activity, which is set at 100%.

EXAMPLES 60-61 & COMPARATIVE EXAMPLE 8

Co-stimulatory Molecule Expression Assays (CD86)

Figure 17A:
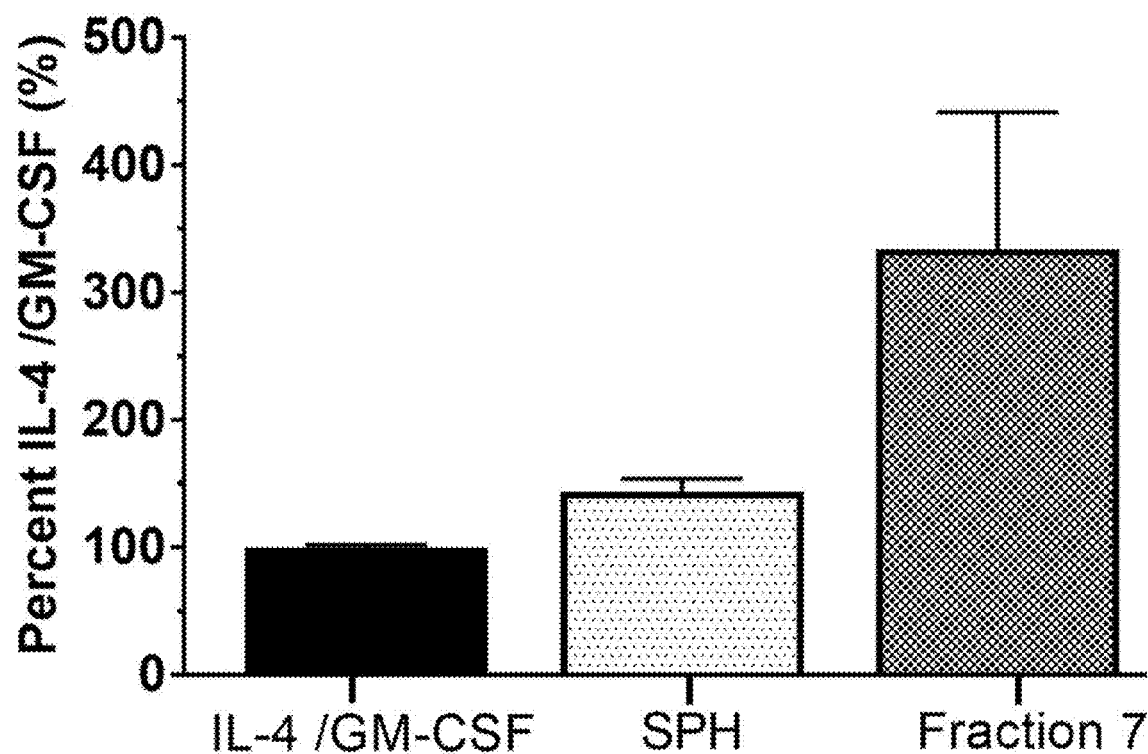
FIGS. 17A and 17B provide results of a Cluster of Differentiation 86 (CD86) assay performed on protein hydrolysate compositions prepared in accordance with the subject disclosure, with FIG. 17A showing relative CD14 assay results of two protein hydrolysate compositions, and FIG. 17B showing relative CD86 assay results of isolated peptides of SEQ ID NOS 1-4, respectively, in order of appearance from left to right.

The procedure set forth above for Examples 54-55 is repeated with additional samples (crude hydrolysate (SPH) and the protein hydrolysate composition of Fraction 7 of Example 1) at a concentration of 2 mg/mL each and IL-4 & GM-CSF at a concentration of 500 µg/mL for 5 days, and then stained with Alexa Fluor® 488 anti-human CD86 antibody. The results of the CD86 assays showing the activity of the samples on IL-4/GM-CSF induced CD86 expression are set forth in FIG. 17A, where data are expressed as a percent of IL-4/GM-CSF treatment activity, which is set at 100%.

EXAMPLES 62-65 & COMPARATIVE EXAMPLE 9

Individual Co-stimulatory Molecule Expression Assays (CD86)

Figure 17B:
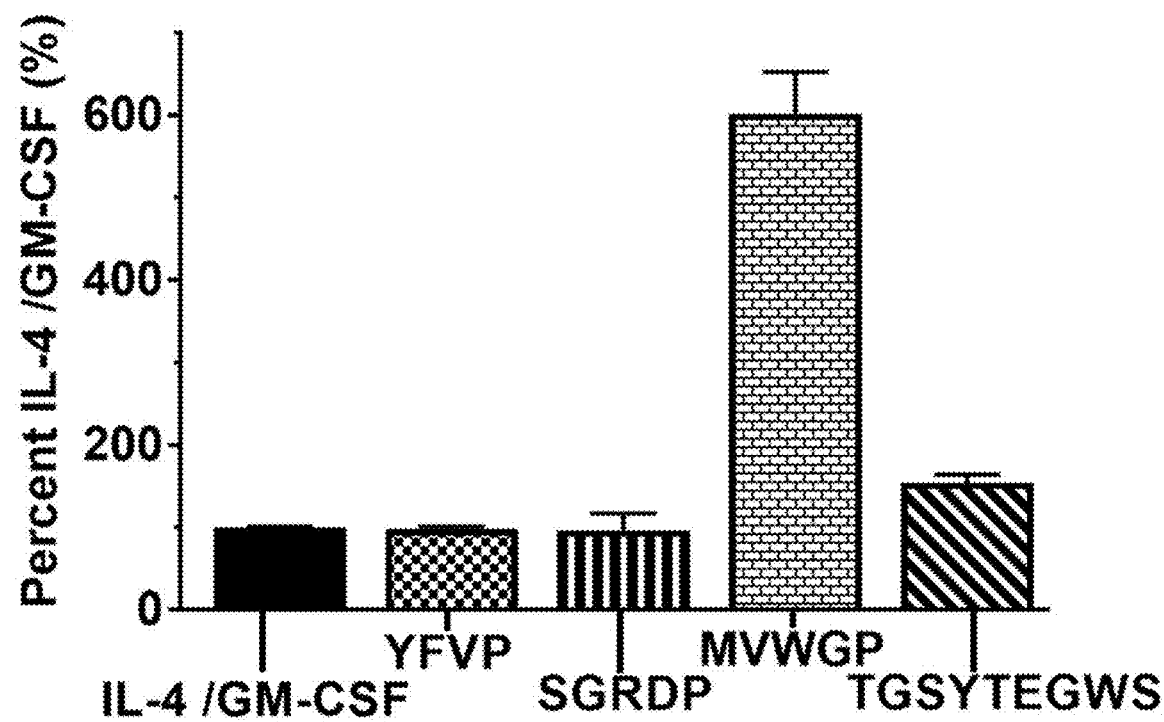

The procedure set forth above for Examples 60-61 is repeated using samples containing one of the isolated peptides 1-4 of Fraction 7 of Example 1 at concentrations of 2.5 mg/mL. The results of the CD86 assays showing the activity of the samples on IL-4/GM-CSF induced CD86 expression are set forth in FIG. 17B, where data are expressed as a percent of IL-4/GM-CSF treatment activity, which is set at 100%.

As demonstrated by the Examples and as shown throughout the Figures, the embodiments of the protein hydrolysate composition of this disclosure comprise improved inflammatory-modulating and immune-modulating properties. In particular, the protein hydrolysate composition suppresses/blunts IL-1β-stimulated NFκKB activation. The protein hydrolysate composition also promotes/boosts IL-4/GM-CSF-induced expression of surface markers CD14 and CD86. As such, the protein hydrolysate composition is shown to have activity indicative of promoting/inducing differentiation/maturation of immature dendritic cells (iDCs) into a mature dendritic cell (DC) phenotype. Accordingly, the protein hydrolysate composition may be used to modulate immunity and/or inflammation (e.g. by inhibiting/decreasing certain inflammation pathways/responses, increasing DC-maturation-related signal/receptor expression/activation, enhancing adaptive immune response to pathogens, etc.), and thus for ameliorating a condition in a subject involving immunity, inflammation, and/or any of the other characteristics or conditions described herein (e.g. inflammatory bowel conditions, etc.).

The present invention has been described herein in an illustrative manner, and it is to be understood that the terminology that has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

The terms "comprising" or "comprise" are used herein in their broadest sense to mean and encompass the notions of "including," "include," "consist(ing) essentially of," and "consist(ing) of." The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A kit comprising a combination of a pharmaceutical agent and a sunflower seed protein hydrolysate composition; wherein the sunflower seed protein hydrolysate composition comprises at least one isolated peptide; wherein the at least one isolated peptide consists of the peptide selected from the group consisting of SEQ ID NO: 1, SEQ ID NO: 2, SEQ ID NO: 3, and SEQ ID NO: 4; and wherein the pharmaceutical agent comprises an angiotensin converting enzyme (ACE) inhibitor.

2. The kit according to claim 1, wherein the sunflower seed protein hydrolysate composition comprises at least two different isolated peptides, and wherein each of the isolated peptides independently consists of the peptide selected from the group consisting SEQ ID NO: 1, SEQ ID NO: 2, SEQ ID NO: 3, and SEQ ID NO: 4.

3. The kit according to claim 2, wherein the sunflower seed protein hydrolysate composition comprises an isolated peptide consisting of the peptide of SEQ ID NO: 1, an isolated peptide consisting of the peptide of SEQ ID NO: 2, an isolated peptide consisting of the peptide of SEQ ID NO: 3, and an isolated peptide consisting of the peptide of SEQ ID NO: 4.

4. A kit comprising a combination of a pharmaceutical agent and a sunflower seed protein hydrolysate composition: wherein the sunflower seed protein hydrolysate composition comprises at least one isolated peptide; wherein the at least one isolated peptide consists of the peptide selected from the group consisting of SEQ ID NO: 1, SEQ ID NO: 2, SEQ ID NO: 3, and SEQ ID NO: 4; and wherein the pharmaceutical agent comprises an anti-inflammatory medication.

5. The kit according to claim 4, wherein the sunflower seed protein hydrolysate composition comprises at least two different isolated peptides, and wherein each of the isolated peptides independently consists of the peptide selected from the group consisting SEQ ID NO: 1, SEQ ID NO: 2, SEQ ID NO: 3, and SEQ ID NO: 4.

6. The kit according to claim 5, wherein the sunflower seed protein hydrolysate composition comprises an isolated peptide consisting of the peptide of SEQ ID NO: 1, an isolated peptide consisting of the peptide of SEQ ID NO: 2, an isolated peptide consisting of the peptide of SEQ ID NO: 3, and an isolated peptide consisting of the peptide of SEQ ID NO: 4.

7. A kit comprising a combination of a pharmaceutical agent and a sunflower seed protein hydrolysate composition; wherein the sunflower seed protein hydrolysate composition comprises at least one isolated peptide; wherein the at least one isolated peptide consists of the peptide selected from the group consisting of SEQ ID NO: 1, SEQ ID NO: 2, SEQ ID NO: 3, and SEQ ID NO: 4; and wherein the pharmaceutical agent comprises a vasodilator.

8. The kit according to claim 7, wherein the sunflower seed protein hydrolysate composition comprises at least two different isolated peptides, and wherein each of the isolated peptides independently consists of the peptide selected from the group consisting SEQ ID NO: 1, SEQ ID NO: 2, SEQ ID NO: 3, and SEQ ID NO: 4.

9. The kit according to claim 8, wherein the sunflower seed protein hydrolysate composition comprises an isolated peptide consisting of the peptide of SEQ ID NO: 1, an isolated peptide consisting of the peptide of SEQ ID NO: 2, an isolated peptide consisting of the peptide of SEQ ID NO: 3, and an isolated peptide consisting of the peptide of SEQ ID NO: 4.

10. A kit comprising a combination of a pharmaceutical agent and a sunflower seed protein hydrolysate composition; wherein the sunflower seed protein hydrolysate composition comprises at least one isolated peptide; wherein the at least one isolated peptide consists of the peptide selected from the group consisting of SEQ ID NO: 1, SEQ ID NO: 2, SEQ ID NO: 3, and SEQ ID NO: 4; and wherein the pharmaceutical agent comprises an immune modulating agent.

11. The kit according to claim 10, wherein the sunflower seed protein hydrolysate composition comprises at least two different isolated peptides, and wherein each of the isolated peptides independently consists of the peptide selected from the group consisting SEQ ID NO: 1, SEQ ID NO: 2, SEQ ID NO: 3, and SEQ ID NO: 4.

12. The kit according to claim 11, wherein the sunflower seed protein hydrolysate composition comprises an isolated peptide consisting of the peptide of SEQ ID NO: 1, an isolated peptide consisting of the peptide of SEQ ID NO: 2, an isolated peptide consisting of the peptide of SEQ ID NO: 3, and an isolated peptide consisting of the peptide of SEQ ID NO: 4.

13. A kit comprising a combination of a pharmaceutical agent and a sunflower seed protein hydrolysate composition; wherein the sunflower seed protein hydrolysate composition comprises at least one isolated peptide; wherein the at least one isolated peptide consists of the peptide selected from the group consisting of SEQ ID NO: 1, SEQ ID NO: 2, SEQ ID NO: 3, and SEQ ID NO: 4; and wherein the pharmaceutical agent comprises a drug used against pain and/or infection.

14. The kit according to claim 13, wherein the sunflower seed protein hydrolysate composition comprises at least two different isolated peptides, and wherein each of the isolated peptides independently consists of the peptide selected from the group consisting SEQ ID NO: 1, SEQ ID NO: 2, SEQ ID NO: 3, and SEQ ID NO: 4.

15. The kit according to claim 14, wherein the sunflower seed protein hydrolysate composition comprises an isolated peptide consisting of the peptide of SEQ ID NO: 1, an isolated peptide consisting of the peptide of SEQ ID NO: 2, an isolated peptide consisting of peptide of SEQ ID NO: 3, and an isolated peptide consisting of the peptide of SEQ ID NO: 4.

\* \* \* \* \*